(12) United States Patent
Lukaszew et al.

(10) Patent No.: US 8,143,072 B2
(45) Date of Patent: Mar. 27, 2012

(54) SYSTEM FOR DETECTING NANOPARTICLES USING MODULATED SURFACE PLASMON RESONANCE

(75) Inventors: Rosa A. Lukaszew, Williamsburg, VA (US); Xuefei Huang, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 758 days.

(21) Appl. No.: 12/278,655

(22) PCT Filed: Feb. 7, 2007

(86) PCT No.: PCT/US2007/003581
§ 371 (c)(1),
(2), (4) Date: Aug. 7, 2008

(87) PCT Pub. No.: WO2008/123844
PCT Pub. Date: Oct. 16, 2008

(65) Prior Publication Data
US 2010/0164489 A1    Jul. 1, 2010

Related U.S. Application Data

(60) Provisional application No. 60/771,320, filed on Feb. 8, 2006.

(51) Int. Cl.
*G01N 33/551* (2006.01)
*G01N 33/553* (2006.01)

(52) U.S. Cl. .......... 436/524; 422/82.11; 435/287.2; 435/288.7; 435/808; 436/525; 436/526; 436/805

(58) Field of Classification Search ........ None
See application file for complete search history.

(56) References Cited

U.S. PATENT DOCUMENTS

| | | | | |
|---|---|---|---|---|
| 4,335,094 | A | * | 6/1982 | Mosbach ............ 424/1.37 |
| 5,691,208 | A | * | 11/1997 | Miltenyi et al. ........ 436/526 |
| 2003/0113582 | A1 | | 6/2003 | Litvinov et al. |
| 2004/0052729 | A1 | | 3/2004 | Penades et al. |
| 2004/0253138 | A1 | | 12/2004 | Malak |
| 2005/0025797 | A1 | | 2/2005 | Wang et al. |
| 2005/0142605 | A1 | | 6/2005 | Malak |
| 2005/0164169 | A1 | | 7/2005 | Malak |
| 2005/0171433 | A1 | | 8/2005 | Boppart et al. |
| 2005/0186565 | A1 | | 8/2005 | Malak |
| 2005/0282219 | A1 | | 12/2005 | Prober et al. |
| 2005/0282220 | A1 | | 12/2005 | Prober et al. |
| 2005/0287681 | A1 | * | 12/2005 | Nishiuma et al. ........ 436/524 |
| 2006/0121040 | A1 | | 6/2006 | Kunnimalaiyaan et al. |

FOREIGN PATENT DOCUMENTS

| | | | |
|---|---|---|---|
| WO | WO 2005121754 | A1 * | 12/2005 |
| WO | WO2006118677 | | 11/2006 |

OTHER PUBLICATIONS

Abe et al., "Magneto-optical enhancement by surface plasmon resonance in magnetic nano-onions with multicore-shell structures," Journal of Applied Physics, vol. 97, Issue 10, May 2005, Abstract.
Kerr, "The Interaction of Electromagnetic Radiation With Magnetic Media", http://www.qub.ac.uk/schools/SchoolofMathematicsandPhysics/con/magnetics_group/magnetoptics.html, Nov. 13, 2008, pp. 1-9.
Intenational Search Report, PCT/US07/03581, Dec. 11, 2008.
International Search Report and Written Opinion, PCT, International Application No. PCT/US06/09949 filed Mar. 17, 2006.

\* cited by examiner

*Primary Examiner* — Chris L Chin
(74) *Attorney, Agent, or Firm* — MacMillan, Sobanski & Todd, LLC

(57) ABSTRACT

A method and system for detecting magnetic nanoparticles include measuring a magneto-optical enhancement of the plasmon absorption in the optical response.

18 Claims, 14 Drawing Sheets

$$k_{xp} = \frac{2\pi}{\lambda}\sqrt{\varepsilon_p}\sin\theta$$

FIG. 13a  FIG. 13b

[a]Reagents and Conditions: (1) N-hydroxysuccinimide, N-(3-dimethylaminopropyl)-N-ethyl-carbodiimide hydrochloride (EDC), CH$_2$Cl$_2$, rt; (2) triethylamine, dimethylformamide, rt, ACA for compound 5, diACA 6 for compound 7; (3) TFA/H$_2$O (1:1), rt aReagents and Conditions: (1) APTES, EDC, CH$_2$Cl$_2$, rt; (2) NHS, EDC, CH$_2$Cl$_2$, rt; (3) triethylamine, dimethylformamide, rt, ACA for compound 9, amino acid 6 for compound 12, amino acid 7 for compound 13.

US 8,143,072 B2

SYSTEM FOR DETECTING NANOPARTICLES USING MODULATED SURFACE PLASMON RESONANCE

This application claims the benefit of U.S. Provisional Application No. 60/771,320, filed Feb. 8, 2006, and International Application No. PCT/US07/003581 filed Feb. 7, 2007. The disclosures of both applications are fully and expressly incorporated herein by reference.

BACKGROUND OF THE INVENTION

There is a need for the improved detection of a wide variety of analytes. Specific analytes for which there is a critical testing needed include pathogenic agents and microbes. Broad clinical use of such a system would assist in identifying diseases or serious illnesses, greatly assisting physicians in diagnosis.

Improved detection is also needed in agriculture and food production, as well as a means to detect contamination, spoiling, or poisoning of food. Food includes for example, items such as drinking water and fruit juices.

In one example, pathogenic bacteria, such as *Escherichia coli* (*E. coli*), can contaminate food and beverages, causing infection outbreaks with serious consequences. The Centers for Disease Control and Prevention (CDC) estimates that 73,000 cases of *E. coli* infection occur annually in the United States. Over 2,000 people are hospitalized every year and over 60 people die as a direct result of *E. coli* infections and resulting complications.

In developing countries and localities of poor sanitation, the threat of *E. coli* is even more severe. One potential reason for the outbreaks is the absence of adequate food and water testing before public consumption. Currently, clinical detection of pathogenic bacteria often relies on culturing the bacteria from a suspected contaminated sample, which can take several days. As such, there is a pressing need for the development of rapid, convenient and sensitive techniques for pathogen detection.

Many pathogens use human cell surface carbohydrates as anchors to facilitate their attachment, which subsequently results in infection. For instance, influenza viruses bind with epithelial cell surface sialic acid in the respiratory tract, while *E. coli* is known to recognize mannose and galactose. In addition, one challenging aspect of studying carbohydrate and pathogen interaction is the low affinity of oligosaccharides to their protein receptor(s). Increasing the valency of an oligosaccharide ligand by simultaneously involving multiple copies of the oligosaccharide can markedly enhance its affinity towards the receptor.

There is also a need for a system to detect analytes that is not subjected to interference from clutter and/or near neighbor molecules. There is also a need for the system to have a low cost, low false alarms and high probability of detection. There is also a need to accurately measure amounts of analyte concentrations in the sample being tested.

Also, there is a need in forensic testing, including for example, searching for specific DNA sequences in a sample at the search site. For example, a system is needed to detect biological agents and toxins to provide early alert in case of a terrorist attack.

Further, in many industrial processes, it is desirable to measure and analyze the concentration of trace species in flowing gas streams and liquids with a high degree of speed and accuracy. Such measurement and analysis is required when the concentration of contaminants is critical to the quality of the end product, but may still be desirable even when not required. Such a system would enable leak detection, process control, detection of material degradation, control of concentration, and a host of other process applications in a wide range of industries.

A compact and automated instrument is desired to rapidly detect the presence of such analytes in the field, rather than requiring that samples be sent to a remote, or off-site, location for testing.

Magnetic nanoparticles (MNPs) have been extensively employed in biomedical research for magnetic separation, targeted drug delivery, protein and DNA purification, and contrast enhancement in magnetic resonance imaging (MRI). The detection of MNPs is typically monitored by transmission electron microscopy (TEM), superconducting quantum interference device (SQUID) magnetometry or MRI, which are limited by access to such expensive and cumbersome equipment.

There is, therefore, a need for an efficient and easy to use system for detecting agents in an environment that is not dependent on these expensive cumbersome methods.

SUMMARY OF THE INVENTION

According to one broad aspect, there is provided a system for detecting magnetic nanoparticles (MNPs) in using a modulated surface plasmon resonance (MSPR) system.

A method and system for detecting magnetic nanoparticles include measuring a magneto-optical enhancement of the plasmon absorption in the optical response. In one aspect, the magnetic metallic nanoparticles are implanted in a matrix. The matrix has a magneto-optically active surface. The magneto-optical and plasmon-like resonance properties of the MNPs can be characterized using, for example, optical reflection in Kretschmann configuration as well as magneto-optical reflection (Kerr effect) and/or transmission (Faraday effect) geometry configurations.

In a particular aspect, the Kretschmann geometry configuration is useful where the MNPs are embedded on a thin film, and the thin film is grown on a substrate. Using the Kretschmann configuration, the enhanced magneto-optical properties are detected using fixed frequency light (for example, He—Ne light with variable incidence angle). Alternatively, frequency dependent measurements at a fixed angle can be used so that the plasmon enhanced magneto-optical properties in the ion-implanted film are identified. One non-limiting method for implanting the nanoparticles on the thin film is the use of an ion-implantation process.

In another particular aspect, the Faraday effect transmission configuration is useful to detect MNPs in a suspension. Using the Faraday effect configuration, the magneto-optical properties are detected by mixing MNPs with a suitable medium having one or more agents to be detected may be present in the medium. If the agent is present, a nanoparticle-agent complex is formed. The complex is magnetically separated from the medium and a magneto-optical response of the nanoparticle-pathogen complex is measured. In one non-limiting embodiment, the method is useful for detecting pathogenic cells in a medium.

In another aspect, there is provided a magneto-optical sensor with a magneto-optically active surface. The magneto-optically active surface has MNPs embedded in a matrix and also has additional dosed MNPs. In certain embodiments, the dosed MNPs are glyco-nanoparticles that are capable of binding to pathogens.

There is also provided a method for detecting magnetic glyco-nanoparticles by measuring a spectral magneto-optical response ($\theta_K$ vs v) of the magnetic glyco-nanoparticles using a magneto-optical effect. In certain embodiments, the magneto-optical effect is measured at a varying incident angle at a fixed frequency in Kretschmann reflection geometry.

In another broad aspect, there is disclosed herein a sensitive and broadly applicable biological detection system which uses nanoscale phenomena.

In a particular aspect, there is provided a system for detecting MNPs that includes measuring plasmon enhancement of a magneto-optical response in one or more nanoparticles. The system for detecting MNPs can include implanting one or more magnetic metallic nanoparticles in a matrix to form a modulated surface plasmon resonance material capable of allowing the magnetic metallic nanoparticles to exhibit plasmon-like resonances and magnet-optical properties.

The system can include a material configured for measuring a plasmon enhancement of a magneto-optical response. The system can also include an array having nanoclusters of MNPs embedded on a metallic thin film matrix. The detecting of the MNPs can include characterizing one or more of surface plasmon resonance (SPR) and magneto-optical (MO) properties of the nanoparticles. The magnetic and MO properties can be characterized by: measuring reflection geometries using fixed frequency light with variable incidence angle; and, finding an optimum frequency for observation of a plasmon-enhanced magneto-optical effect using spectral determination of $\theta_{Kerr}$.

The system can include detecting magneto-optical rotation that is enhanced due to plasmon resonance or plasmon absorption that is enhanced due to magneto-optical coupling, where one or more of the shape and amplitude of the plasmon resonance are affected by one or more of a size and shape of a transition metal inclusion.

In another particular aspect, there is provided herein a system for detecting the presence of pathogenic cells in a medium believed to contain one or more pathogenic cells. The system can include: mixing magnetic glyco-nanoparticles with the medium, whereby a glyco-nanoparticle-pathogen complex is formed if any pathogenic cells are present in the medium; separating the glyco-nanoparticle-pathogen complex from the media; and, measuring a magneto-optical response of the glyco-nanoparticle-pathogen complex.

In yet another particular aspect, there is provided herein a system that uses a glyco-nanoparticle-pathogen complex as an anti-infectious agent. The system can include: mixing magnetic glyco-nanoparticles with at least one medium believed to contain cells of one or more pathogenic agents (whereby the magnetic glyco-nanoparticles attach to cells of the pathogenic agent), and separating the cells from the medium.

In still another particular aspect, there is provided herein a system device for evaluating one or more of magnetic, optical and magneto-optical (MO) characterizations using magneto-optical and optical effects. The system can include: a device for measuring reflection geometries using fixed frequency light with variable incidence angle; and, a device for finding an optimum frequency for observation of a plasmon-enhanced magneto-optical effect using spectral determination of $\theta_{Kerr}$ in reflection geometry.

The system can further include a device configured for optical absorption in reflection that is enhanced due to magneto-optical coupling, where the shape and amplitude of the plasmon resonance are affected by one or more of a size and shape of a ferromagnetic transition metal inclusion.

In another particular aspect, there is provided herein a system for detecting magnetic glyco-nanoparticles that includes: a device configured for measuring a spectral magneto-optical response ($\theta_{Kerr}$ vs v) of the glyco-nanoparticles using a magneto optical effect; a device configured for measuring an incident angle in reflection Kretschmann geometry; and, a device configured for characterizing the magneto-optical response of the magnetic glyco-nanoparticles in a medium using a magneto-optical effect to determine transmission geometry.

In another particular aspect, there is provided herein a system for the functionalization of MNPs with organic molecules using a direct attachment approach.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE FIGURES

FIG. 13a shows TEM image of uncoated MNPs.

FIG. 13b shows images of MNPs coated with rhodamine B.

FIG. 15a shows a method for preparing the linker N-Boc-6-diACA 5; and FIG. 15b—a method for preparing a linker a diCA 6.

FIG. 21b shows the IR spectra of glucosamine 14 (trace I) and glucosamine 14 coated MNPs (trace II).

DESCRIPTION OF THE INVENTION

Figure 1:
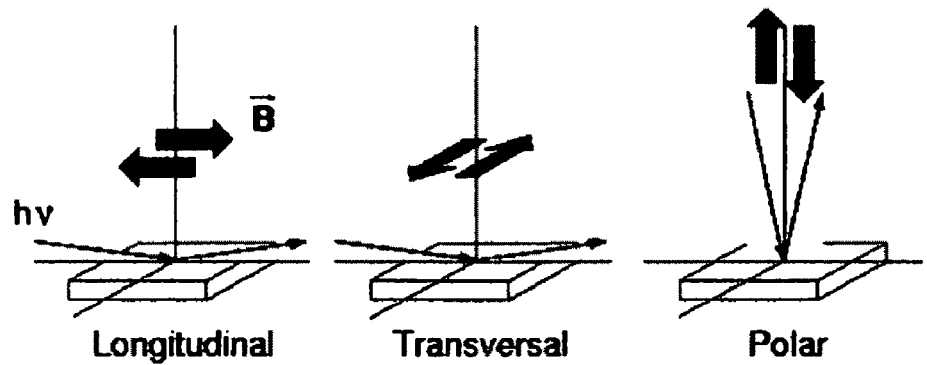
FIG. 1 is a schematic illustration showing three possible magneto-optical effects in reflection geometry (Kerr effect).

A system and method are provided which can detect target analytes based on surface plasmon resonance (SPR) and magneto-optical (MO) measurements. In one aspect, analytes are detected using specific nanoparticles.

The term "analyte" generally refers to a substance to be detected or assayed by the system described herein. In one aspect, there is provided a system and method for detecting analytes in a liquid medium. In another aspect, analytes may be detected in other media, including, but not limited to air, aerosols and complex media such as soil, food, bodily fluids, and the like. It is to be understood that the media can contain one or more analytes. Here "contains" means that the analyte is dissolved, suspended, emulsified, or otherwise wholly enclosed in and dispersed within the medium.

The analyte can be any molecule, molecular complex, microbe, chemical, or material that can be formed into a "magnetic analyte-nanoparticle complex", as further described herein. Typical analytes may include, but are not limited to, biological cells, microorganisms, cellular organelles, cell membrane fragments, bacteriophage, bacteriophage fragments, whole viruses, viral fragments, proteins, peptides, nucleic acids, peptide nucleic acids, antibodies, receptors, molecules, and the like.

The terms "target" and "target analyte" generally refers to the analyte targeted by the detection system described herein. In certain embodiments, the sources of targets will typically be isolated from organisms and pathogens such as viruses and bacteria or from an individual or individuals, including but not limited to, for example, blood, plasma, serum, spinal fluid, lymph fluid, synovial fluid, urine, tears, blood cells, skin, organs, tumors, and also to samples of in vitro cell culture constituents (including, but not limited to, a medium containing cells in a cell culture medium, recombinant cells, cell components and the like). Additionally, targets may be from synthetic sources.

Specific examples of analytes include bio-molecules such as pathogens, small molecules, organisms, microbes such as whole or disrupted viruses or bacteria; whole or disrupted cells from other species including humans, proteins, DNA, RNA, or fragments or complexes thereof; enzymes, non-biological chemicals such as industrial chemicals, chemical weapon molecules, explosives, insecticides, pharmaceuticals, and the like.

The systems and methods described herein are useful to detect targeted analytes with very high specificity, despite near-neighbor interferences such as environmental interferents such as dust or dirt, biological interferents such as mold spores, proteinaceous interferents, paramagnetic interferents such as hemoglobin, and the like.

In contrast to most current sensing schemes that use a "passive" surface plasmon resonance process that is simply based on changes in optical properties of a noble metal surface, the present system described herein has an "active" modulated surface plasmon resonance (MSPR) system that has optical properties that can be varied. The optical properties can be varied by the application of an external magnetic field. The active MSPR surfaces allow for the development of modulated and, therefore, more sensitive detection systems. The magnetic nanoparticle embedded on a matrix is an "active" structure because the magnetization state can be changed by an external magnetic field.

In one aspect, MNPs are embedded in a suitable matrix that forms an active MSPR surface. The active MSPR surface is useful as a biological sensor by using surface plasmon resonance (SPR) and magneto-optical enhancement.

There is also provided herein methods for making active MSPR surfaces that exhibit optimal magneto-plasmonic properties useful as sensors for one or more targets, or agents of interest, in an environment to be tested.

In one embodiment, the MSPR surfaces are used in a system for sensitive detection on one or more agents of interest. The MSPR system uses a combination of "active" MNPs: i) functionalized coated MNPs; and ii) an active MSPR surface that includes MNPs embedded in a noble metal (e.g. silver, gold, platinum, palladium and their alloys) matrix. The active MSPR surface is then dosed with the functionalized coated MNPs to form a composite MSPR material.

The functionalized coated MNPs are added to a medium or environment that may contain the targets. If the targets are present, the functionalized coated MNPs bind with the targets. Upon binding with the targets, the MNPs are attracted and anchored to the embedded MNPs in the magneto-optical sensor surface due to the magnetic dipolar interaction.

The binding of the nanoparticles to the targets is sensed using an optical method that is based upon plasmon enhancement of the magneto-optical response of the composite surface. By discriminating between: i) the change in the magneto-optical activity due to anchored nanoparticles attached to the targets, and ii) the change due to anchored nanoparticles, the resulting active nanostructured surface thus serves as a sensitive detector.

In certain non-limiting embodiments, the functionalized coated MNPs are "sugar coated" MNPs (glyco-nanoparticles). The targets can be microbes or other agents of interest. In a particular embodiment, the target can be, for example, biological pathogens. Many pathogens use human cell surface carbohydrates as anchors to facilitate the pathogen's attachment to the cell surface. This pathogen attachment subsequently results in infection. For instance, influenza viruses bind with the epithelial cell surface sialic acid in the respiratory tract, while E. coli is known to recognize mannose and galactose on other cell surfaces.

Thus, according to one system disclosed herein, magnetic glyco-nanoparticles are useful as a versatile platform for a multivalent display of carbohydrates. The carbohydrates, in turn, bind with the target with high affinity. Moreover, an array of glyco-nanoparticles, each bearing a unique carbohydrate structure, can be assembled to allow for detection of the target with high specificity.

In a particular aspect, the present system is especially useful for the detection of bacteria in an environment to be tested. Bacteria are generally large (micrometer range) and are capable of binding multiple glyco-nanoparticles on their exterior surfaces. Any change in the magneto-optical activity due to the anchored nanoparticles that have attached thereto the bacteria as compared to any change due to bacteria-free anchored nanoparticles is then detected. In the localized surface plasmon (LSP) of the MSPR material, the charge density oscillations are confined to metallic nanoparticles. In addition, the capability of modulated detection due to a localized surface plasmon (LSP) enhanced optical response provides a biosensor system with a much higher sensitivity than currently available in other bio-sensors.

It is to be understood that the choice of materials, the particle size and separation methods will affect the magnetic and magneto-optical behavior of embedded arrays of MNPs in the active MSRP surface. In addition, the environment surrounding the nanoparticles plays a role. Even if the surrounding environment is non-magnetic, it may be polarized, thus affecting the global behavior of the system.

In certain embodiments, there is provided a system for the synthesis and development of magnetic glyco-nanoparticles that are target-specific and/or target-sensitive. The magnetic glyco-nanoparticles are useful with the enhanced magneto-optical surface as novel bio-sensors.

In another aspect, there is provided an array comprised of MNPs embedded in a noble metal matrix. The arrays are useful as bio-detection systems. Also, the MNPs present an attractive platform for the multivalent display of oligosaccharides that can be used as an array for testing for multiple targets.

Significant enhancement of the MO response and signal-to-noise ratio is achieved from MNPs that are deposited near transition or noble metal matrices such as, for example, gold, silver and platinum. In certain non-limiting embodiments, the MNPs, in conjunction with the noble metals matrices, are formed into a highly sensitive and portable MO article.

While the noble metals are non-ferromagnetic and ferromagnetic materials suffer from strong plasmon damping, it has been surprisingly discovered that the metallic nanoparticle MSRP material (made of noble metals and ferromagnetic metallic nanoparticles) sustains surface plasmons and has MO activities at the same time. This behavior also occurs in the multilayers of noble metals and ferromagnetic metals, where the ferromagnetic layers broaden the plasmon resonance of the MSRP material and introduces an additional MO activity in the system, which is absent in pure noble metal layers.

Furthermore, MNPs are useful for the determination of transient field-induced birefringence in ferrofluids and in magnetic nanoparticle suspensions by measuring the magneto-optical effects using the Faraday effect transmission geometry configuration as described herein.

The invention will now be illustrated by the following non-limiting examples.

EXAMPLES

Magnetic Nanoparticles (MNPs) and Plasmon-Enhanced MO Properties

Magnetic nanoparticles (MNPs) are embedded on noble metal thin films to form a MSRP material using, for example, ion-implantation or sub-monolayer growth of MNPs onto one or more reconstructed and patterned surfaces. In certain embodiments, films comprised of noble metal thin films (e.g., Au, Ag) are grown on glass substrates and prepared via UHV evaporation and/or sputtering and/or chemical vapor deposition. Other methods to incorporate magnetic nanoparticles to the noble metal matrix can be used such as nanocluster deposition, composite target sputtering, co-sputtering, laser ablation deposition, nanopatterning using for example e-beam lithographic techniques and self-assembly. Upon growth, the films are characterized by X-ray diffraction (XRD) as well as atomic force microscopy (AFM). Ion implantation of $Co^+$ is carried out at an accelerator facility or commercial implanter.

Simulations can be carried out to find the optimum ion-implantation conditions for Co on Au and Ag films by using SRIM (Stopping and Range Ions in Matter free software). After ion-implantation, the films can be annealed in UHV and characterized again with XRD and AFM. Magnetic characterization can be performed by measuring the magneto-optical effects using the reflection geometry configuration; for example, by using fixed frequency light (e.g., He—Ne light). The setup also allows magneto-optical spectral determination of the Kerr rotation, $\theta_K$, as shown in FIG. 1. Magneto-optical scans at varying incident angles can be used to find the optimum angle of incidence for the observation of the plasmon-enhanced reflectometry at fixed frequency. Alternatively, spectral scans with varying frequency can be performed to find the optimal plasmon resonance frequency at a fixed angle.

Figure 2:
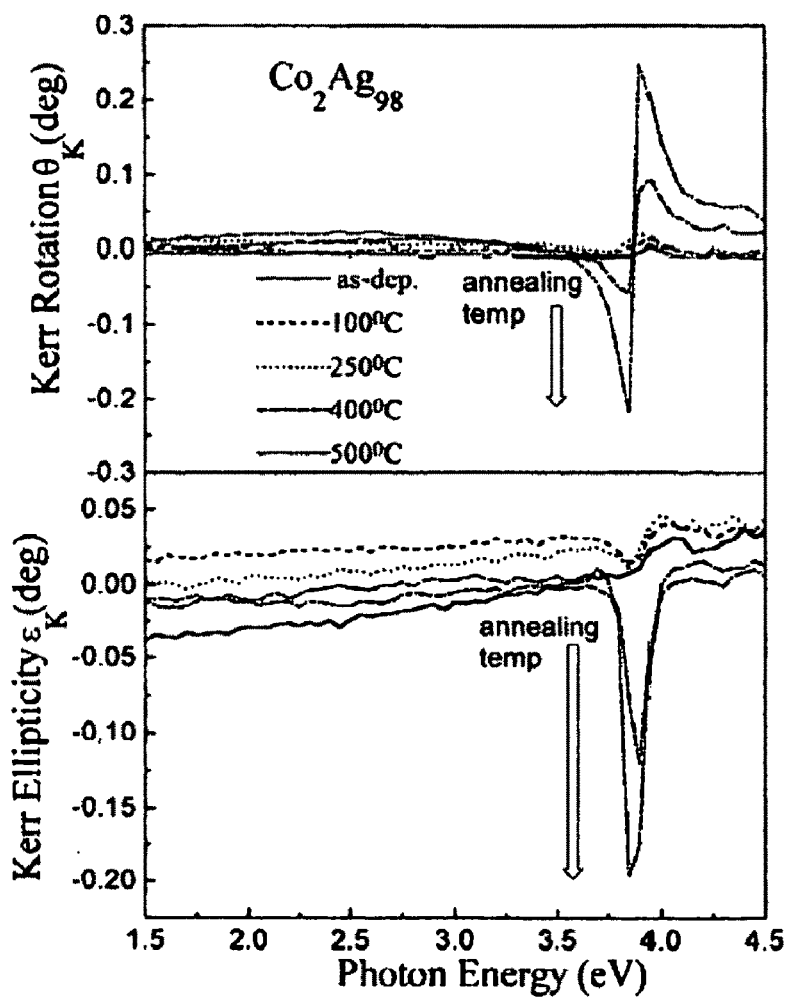
FIG. 2 is a schematic illustration of the magneto-optical spectra in reflection geometry and at a fixed angle measured at room temperature for $CO_2Ag_{98}$ with different annealing temperatures.

FIG. 2 shows computer simulations of the polar Kerr rotation as a function of the incident angle for a layer of Co discs (10 nm diameter) embedded in an Au layer. The polar Kerr rotation is greatly enhanced due to a plasmon resonance. The shape and amplitude of this feature depend on parameters such as size and shape of the transition metal inclusion.

Fabrication of Magneto-Optically Active Sensor Surface

The response $\Delta R_{max}$ of an SPR sensor can be described by the following equation: $\Delta R_{max} = m(n_{ads} - n_{bulk})\exp(-2_{ads}/L_d)[1-\exp(-2_{ads}/L_d)]$ where m is the refractive index sensitivity of the sensor, $n_{ads}$ and $n_{bulk}$ are the refractive indices of the desired adsorbate and bulk environment prior to the sensing event, respectively, $d_{ads}$ is the effective thickness of the adsorbate layer, and $L_d$ is the characteristic electromagnetic field decay length associated with the sensor. Because the typical electromagnetic field decay length (~6 nm) in nanoparticles is significantly shorter than the corresponding length (~200 nm) for a flat surface, MNPs embedded in noble metals provide "active sites" with considerably larger magneto-optical activity and sensitivity than for a flat multilayered surface.

In one embodiment, the noble metal matrix provides a large refractive index for the integrated sensor as compared to the nanoparticles. The combined effects lead to larger sensitivity.

Fabrication of Shallow Arrays of Magnetic Nanoparticles (MNPs) Embedded on a Suitable Matrix.

To preserve the magnetic properties of the nanoparticles, their chemical composition must remain unchanged. Therefore, fabrication methods that promote particle oxidation are not suitable. High temperatures must also be avoided because the nanoparticles can be aggregated into large clusters that may not be acceptable for magneto-optical sensing based on localized surface plasmons (LSP) resonance. Since currently available optical lithographic techniques do not yield particles in the size-range of interest, different fabrication methods are used to fabricate the required composite materials.

In one embodiment, an array of MNPs is formed on a semi-transparent thin-film for magneto-optical sensing. Crystalline Au films are grown on glass at 350° C., which produces crystalline films with a (111) orientation and reconstructed surface. The surface reconstruction can be varied by applying strain to the reconstructed surface. Subsequently, a thin Co film is grown on top of the crystalline Au film followed by the growth of additional Au on the Co surface. The strain between the Co and Au film layers introduces a buried network of dislocations. The subsequent Co sub-monolayer growth on the strained Au surface yields arrays of Co islands or nanostructures. Here, the degree of strain present allows "tunable" inter-island distance which, in turn, affects the magnetic coupling.

Ion-Implantation

The formation of MNPs using ion implantation is discussed in the co-pending application to one of the co-inventors here, Dr. R. A. Lukaszew in Ser. No. 60/676,402, now PCT/US06/009949, which is fully incorporated herein by reference. Briefly, Fe ions implanted on epitaxial Pt films form shallow nanoclusters that, after annealing, self-assemble into a highly ordered phase ($L1_o$) with enhanced magnetic anisotropy as well as magneto-optical properties. For the present method, the implantation parameters (ions, energy and dose) are tuned to achieve shallow penetration and nanocluster formation.

MSPR materials comprised of Co ions-implantation on epitaxial Au thin films show that ion-implantation is a suitable route to obtain arrays of Co nanoclusters embedded on a metallic thin film matrix. Subsequent thermal treatment of the MSPR material is another suitable parameter that can be adjusted in order to tailor the size and inter-particle distance of the nanoclusters.

Materials Characterization

The ex situ structural characterization of the MSPR material can be performed by X-Ray Diffraction (XRD) in order to determine lattice constants, average particle size, residual stress, measurements of film thickness, and identification of surface reconstructions. Additional ex-situ structural characterizations of the MSPR material can be performed by the use of atomic force microscopy (AFM), scanning tunneling microscopy (STM) and cross-sectional transmission electron microscopy (XTEM) to investigate surface morphology, nanoparticle size-distribution and inter-particle distance.

The magnetic characterization of the MSPR material can be performed using Kerr magnetometry (i.e., the polar, transverse and longitudinal Magneto-Optical Kerr Effect (MOKE)) and/or magnetic force microscopy (MFM). Kerr magnetometry evaluates the competition between magnetocrystalline and shape anisotropy in the nanoparticles, as well as size-shape effects and inter-particle separation effects on the magnetization reversal, and thus, on the coupling between particles. MFM yields information on magnetic charges on the surface. The magnetic characterization also provides relevant information about domain structure, i.e., if the nanoparticles behave as a multi-domain or as a single-domain when they are larger than 20 nm. If they are smaller than 20 nm, the magnetic characterization can provide information on magnetic percolation due to dipolar interaction between particles, or exchange interaction due to a light matrix polarization.

The magneto-optical characterization can also involve near field-techniques such as scanning optical microscopy (NSOM). These characterizations evaluate the spatial distribution of the electromagnetic field near the surface under total reflection conditions. Excitation under total reflection allows better coupling between light and the plasmons in the structure. The optimal conditions for surface plasmon excitation and the corresponding distribution of the associated electromagnetic field are also determined. Knowledge of the spatial distribution of the electromagnetic field intensity is useful for employing these materials as magneto-optical sensors for biological applications. The knowledge of the spatial distribution indicates points in the active sited surface where the "glyco-nanoparticles with the bio-agent to be detected" will be anchored, producing a change in the local index of refraction, as further described below.

Characterization of Magneto-Optical Responses

Figure 3:
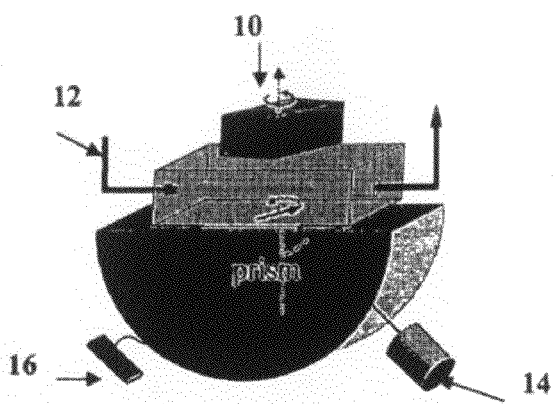
FIG. 3 is a schematic illustration of a modified surface plasmon resonance (SPR) arrangement with modulation for enhanced magneto-optical surface plasmon resonance (SPR) detection.

The "active" films can be characterized using a modulated magneto-optical system that includes a movable magnet 10, a flux cell 12, a laser light 14, and a detector (e.g., diode), as schematically illustrated in FIG. 3. Once the optimum conditions for the detection of plasmon enhanced magneto-optical properties in magneto-active films are determined, the magnetic glyco-nanoparticles are dosed by the Langmuir-Blodgett (LB) technique, or by spin-coating submonolayer films on the substrates to monitor changes on the magneto-optical response.

Figure 4A:
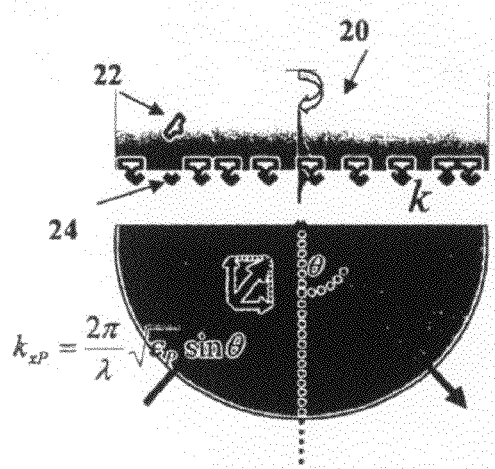
FIG. 4a is a schematic illustration of a modulated SPR sensor where light reflects from a functionalized magneto-plasmonic layer.
Figure 4B:
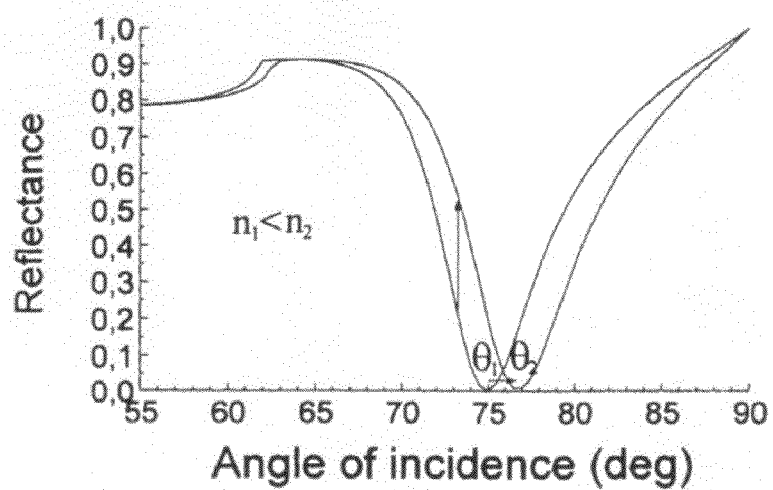
FIG. 4b is a graph showing expected changes in the reflectance curve related to changes in the refractive index at the interfacial surface resulting from binding of magnetic glyco-nanoparticles.

FIG. 4a shows a schematic illustration of a fast switching weak magnetic field 20, magnetic glyco-nanoparticles 22, and a magneto-optical sensor surface 24 of the MSPR material where light reflects from a functionalized magneto-plasmonic layer. FIG. 4b shows the expected changes in the reflectance curve related to changes in the refractive index at the interfacial surface resulting from binding of magnetic glyco-nanoparticles.

In FIG. 4a, a p-polarized light-beam is incident on an "active" surface. For a certain incidence angle, such light beam can excite a surface plasmon that propagates in the interface between the active surface and any liquid medium in which the "active" surface is located. The excitation occurs when the light beam moment is coincident with the surface plasmon ($k_{xp}=K_s$). Under such conditions, there will be a minimum in the metallic layer reflectivity. The position of this minimum reflectivity depends on: i) the refractive index of the liquid medium ($n_i$); and, ii) because the surface plasmon is localized in the interface, also on the refractive index of the liquid in contact with the interface. Since the MNPs are very small they are paramagnetic. As a result, very low magnetic fields are needed to modify their magnetization state and magneto-optical activity. Fast switching of this low magnetic field provides modulation of the detected signal; and thus, improved sensitivity.

The switching rate can be adjusted (kHz range) to be sufficiently fast for magnetization modulation, while avoiding "artifacts" in the detected signal due to induced motion of the glyco-nanoparticles. Thus, when glyco-nanoparticles are anchored on the active site, of the surface, the magnetization switching is faster than any possible motion. Any change in the index of refraction in this region is observed, which in turn changes the reflectivity.

Magneto-Optical (MO) Detection of Pathogens Using Glyco-Nanoparticles

Colloidal heptane solutions of ferromagnetic nanoparticles coated with oleic acid molecules are used to deposit nanoparticle monolayers either by the Langmuir-Blodgett (LB) technique or by spin-coating submonolayer films on the noble metal films with embedded magnetic nano-particles. Bare glass substrates coated with a gold film are used as reference samples and are coated with a LB monolayer of stearic acid prior to deposition of a magnetic nanoparticle monolayer.

Gold or silver coated glass with embedded magnetic nanoparticle substrates are used to deposit glycocoated MNPs at the surface. Exchanging the oleic acid coating layer to dodecenoic acid reduces the separation to the minimal distance possible using the LB technique. All surfaces are imaged using atomic force microscopy (AFM) and magnetic force microscopy (MFM). The magnetic properties are determined using longitudinal and polar magneto-optical Kerr effect (MOKE). The magnetic glyco-nanoparticles bind to the sites where there are embedded magnetic nano-particles in the gold films due to dipolar interaction.

In one non-limiting embodiment, pathogens are detected using magnetic glyco-nanoparticles that are fabricated through the attachment of carbohydrates onto MNPs.

Fabrication of Glyco-Nanoparticles

Thus, in another aspect, there is provided a system for determining the total level of a target or agent of interest in an environment without the time consuming process of antibody generation or traditional growth-based detection methods.

For example, all strains of *E. coli* have adhesion proteins on their cell surfaces. The adhesion proteins can recognize a variety of carbohydrate structures including galactosides and mannosides.

In one non-limiting embodiment, a panel of glyco-conjugates ranging from simple mannosides (see FIG. 5, e.g. 1-3) and galactosides (see FIG. 5, e.g. 4-6) to complex oligosaccharides (see FIG. 5, e.g. 7-9), which have higher affinity with the bacteria, is synthesized as outlined in FIG. 5. One suitable method that can be used is the recently developed iterative one-pot synthesis method, as set forth in the Ser. No. 11/029,917 filed on Dec. 22, 2004, and has Pub. No. 2005/0135485A1 published on Jun. 23, 2005, to one of the co-inventors herein, Dr. Huang, which is fully and expressly incorporated herein by reference. These glyco-conjugates contain a hydrophilic oligoethylene oxide linker terminated by a carboxylic acid for immobilization onto nanoparticles. Carbohydrate structures as well as the length of the linker are readily optimized to optimize detection.

Magnetite nanoparticles (~6 nm diameter) coated with amino silane are prepared by co-precipitation of $Fe^{2+}$ and $Fe^{3+}$ followed by addition of 3-aminopropyl triethoxysilane. Carbohydrates are attached to the nanoparticles through amide bonds forming glyco-nanoparticles, which are purified via magnet-induced precipitation and re-dissolved in water after removal of the magnetic field. This purification step, in combination with the highly hydrophilic nature of glyco-nanoparticles, minimizes the non-specific binding. This provides a high detection sensitivity which is especially desirable for the testing of biological, and in particular, environmental samples.

Synthesis of Magnetic Glyco-Nanoparticles

To demonstrate the application of MO detection in biological systems, magnetic glyco-nanoparticles are synthesized through the attachment of mannosides (e.g., 1-3, 7-9) and galactosides (e.g., 4-6) onto MNPs.

Glycoconjugates containing both hydrophobic (e.g., 1, 4, 7) and hydrophilic linkers (e.g., 2, 3, 5, 6, 8, 9) are useful as hydrophilic linkers that confer higher water solubility, while hydrophobic linkers lead to a more rigid display of the terminal sugar on nanoparticles through hydrophobic interactions.

Treatment of peracetylated D-mannopyranoside with hydrogen bromide in acetic acid followed by $Hg(CN)_2$ promoted glycosylation yields mannosides 10-12. $S_N2$ displacement of the terminal bromide and subsequent deprotection under basic conditions produces fully deprotected mannosyl disulfide 1-3 (FIG. 5). Galactosides 4-6 are prepared analogously (FIG. 5*b*). The immobilization of glycoconjugates onto MNPs is carried out under reductive conditions taking advantage of the high affinity of thiolates with metal atoms (FIG. 5*d*). The magnetic glyco-nanoparticles synthesized are readily soluble in water due to their hydrophilic exterior.

Synthesis of Magnetic Glyco-Nanoparticles Through Two Different Routes

Magnetic glyco-nanoparticles (GNP 2 and GNP 4) were synthesized as outlined in FIG. 6, through two different routes.

For Con A detection experiments, fluorescently labeled Con A was incubated with same amounts of MNP 1, GNP 2 and GNP 4. The nanoparticles were then retrieved from the solution using a magnet. The fluorescent emission spectra of the residual solution after nanoparticle removal were recorded.

Since MNP 1 does not contain any mannoses on the surface, it did not remove any Con A from the solution as indicated by the identical emission intensity of the solution as compared with that of Con A (see FIG. 7). With GNP 2, Con A bound to its surface mannoses thus was removed from the solution as a complex with GNP 2 when the magnetic field was applied. The decrease of emission intensity provided a simple and direct method for detecting the presence of Con A. GNP 4 was more efficient than GNP 2 for detecting Con A judging from the much lower emission intensity from the residual solution, as shown by the graph in FIG. 8.

Nanoparticles Used as Sensors

MNPs with high magneto-optical activity and homogeneous sizes (e.g., Co, FePt) are useful as sensors. The exterior surfaces of many metallic nanoparticles are charged and proteins tend to aggregate nonspecifically on the surface via electrostatic interactions, which reduces the detection sensitivity. This nonspecific binding is essentially eliminated by incorporating ethylene glycol monolayer on the surface of nanoparticles. With the hydrophilic exterior surface of glyco-nanoparticles, nonspecific protein binding is minimal. TEM is used to determine size and homogeneity of the magnetic glyco-nanoparticles.

Multivalent Binding of Glyco-Nanoparticles with a Lectin

The specific binding of oligosaccharide ligand on glyco-nanoparticles with protein receptors is analyzed using lectins (a class of carbohydrate binding proteins). For glyco-nanoparticles encapsulating mannosides 1-3, a tetrameric lectin Con A with four oligosaccharide binding sites is employed. Upon addition of Con A, the glyco-nanoparticles aggregate with Con A through multivalent interactions thereby forming complexes, which complexes can be readily separated from the bulk media using a magnet. With the high magnetization of Co or FePt nanoparticles, small desktop magnets (~3000 Oe) are sufficient for a complete separation. As a control, magnetic glyco-nanoparticles immobilized with galactoside 4-6 are prepared which do not show substantial binding with Con A because nanoparticle immobilization of carbohydrates is not expected to alter lectin specificity.

Referring again to FIG. 7, there is shown the schematic demonstration of complex formation between encapsulated magnetic glyco-nanoparticles and Con A.

The non-covalent binding between Con A and glyco-nanoparticles is reversible and hence can be readily disrupted by a competing ligand to dissociate Con A from the nanoparticles. The efficiency of Con A immobilization is determined by measurement (e.g., Bradford method) of the amount of protein eluted off glyco-nanoparticles with a concentrated solution of a competing mannoside ligand (e.g., 20). Dissociation constants of Con A with glyco-nanoparticles are determined by competitive binding assays with varying concentration of mannoside 20. The optimal linker and density of carbohydrate displayed on glyco-nanoparticles for maximum Con A immobilization is then determined and used in further experiments.

Figure 5:
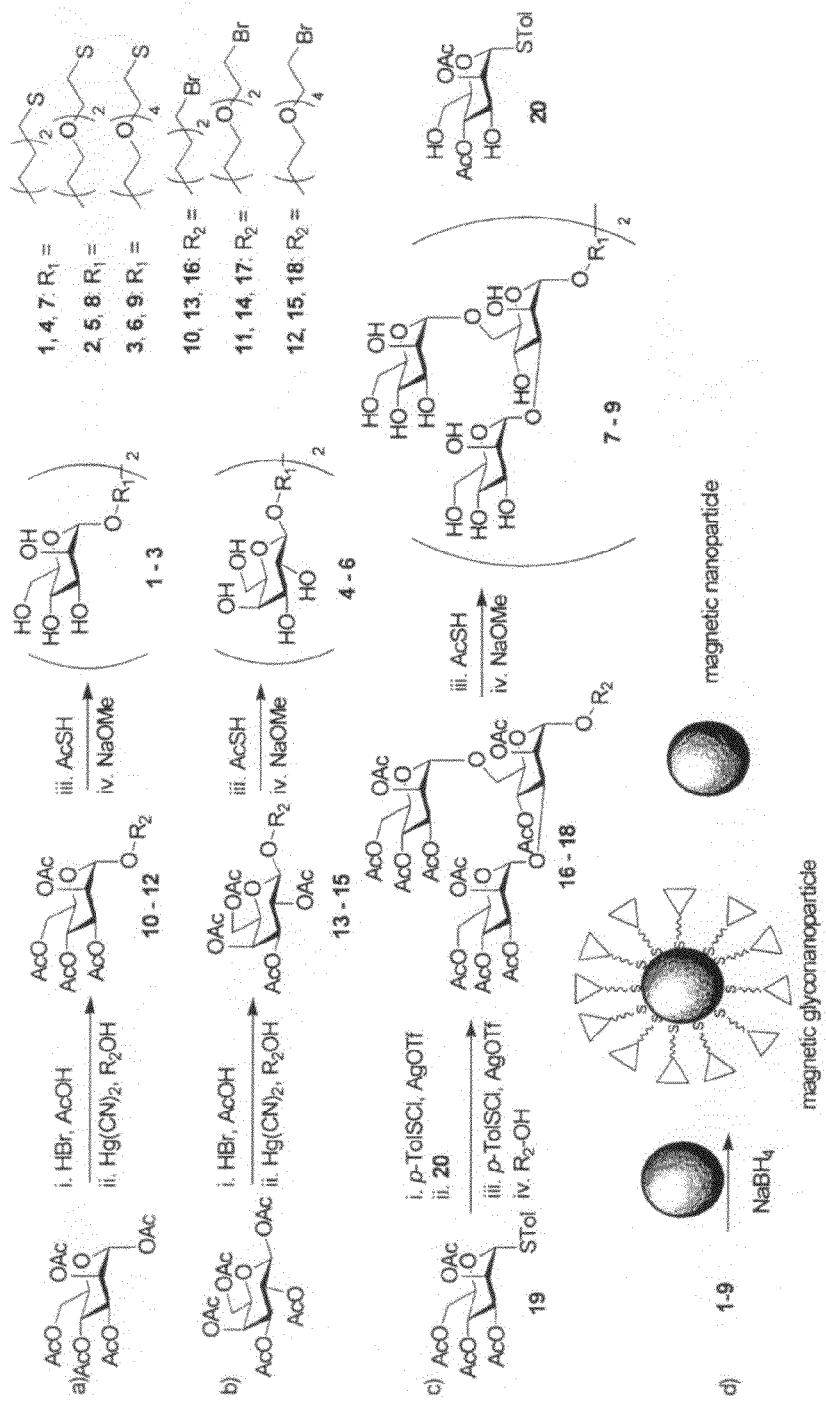
FIG. 5 is a schematic illustration showing the synthesis of glycoconjugates and magnetic glyco-nanoparticles.
Figure 6:
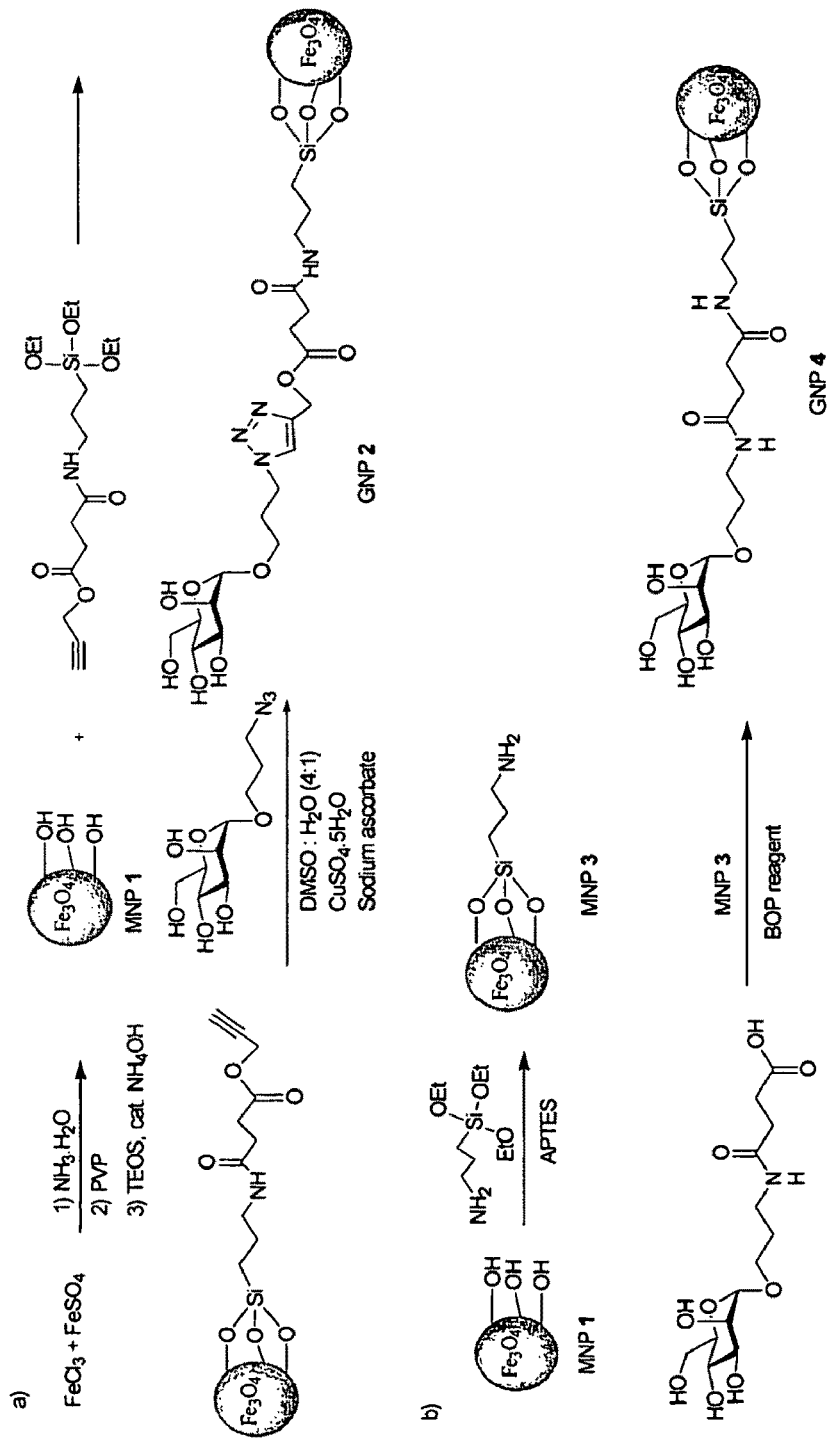
FIG. 6 is a schematic illustration showing two routes of synthesis of glycoconjugates and magnetic glyco-nanoparticles.
Figure 7:
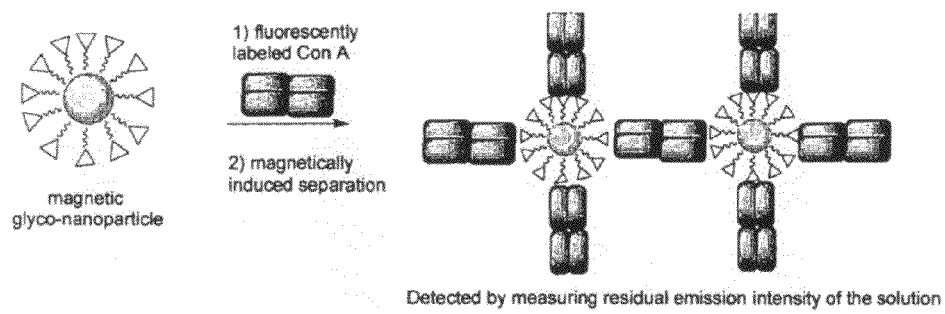
FIG. 7 is a schematic illustration of a complex formation between encapsulated magnetic glyco-nanoparticles and Con A.

In order to improve the binding affinity, larger oligosaccharides (e.g., 7-9), which have higher affinities with Con A than mannoside (e.g., 1-3), are synthesized using an iterative one-pot oligosaccharide synthesis method through pre-activation of the thiomannosyl donor 19 (as shown in FIG. 5c). Glycoconjugates (e.g., 7-9) are incorporated onto FePt nanoparticles in a similar manner as described for mannosides 1-3. The resulting magnetic glyco-nanoparticles provide tighter binding with Con A, resulting in higher detection sensitivity.

Detection of Magnetic Glyco-Nanoparticles

Solutions of magnetic glyco-nanoparticles are used to deposit nanoparticle monolayers onto a substrate such as glass coated with gold films with embedded magnetic nanoparticles. In certain embodiments, the glyco-nanoparticles can be deposited by the Langmuir-Blodgett (LB) technique or by spin-coating submonolayer films on the substrates. The reflectivity of the surface at various angles of incidence is measured and the spectral MO response ($\theta_K$ vs v) is measured using the magneto-optical Kerr effect. A large signal-to-noise ratio is expected because of plasmon enhanced MO properties at the binding sites of the glyco-nanoparticles to the embedded magnetic nano-particles.

The MO response of magnetic glyco-nanoparticles in suspension is characterized using the transmission geometry (the Faraday effect) configuration. This method is especially useful in the evaluation of biological binding reactions in solution.

Upon binding with Con A, the media at the mannose encapsulated glyco-nanoparticle surface change, thus resulting in an altered surface plasmon behavior, and thus affecting the spectral MO response of the nanoparticles. The alteration in spectral MO response of the complex is then calibrated against the amount of Con A determined from an alternative method, such as the Bradford method. The limits of the MO detection method are then determined by modulating the amount of Con A added to the glyco-nanoparticles.

Figure 8:
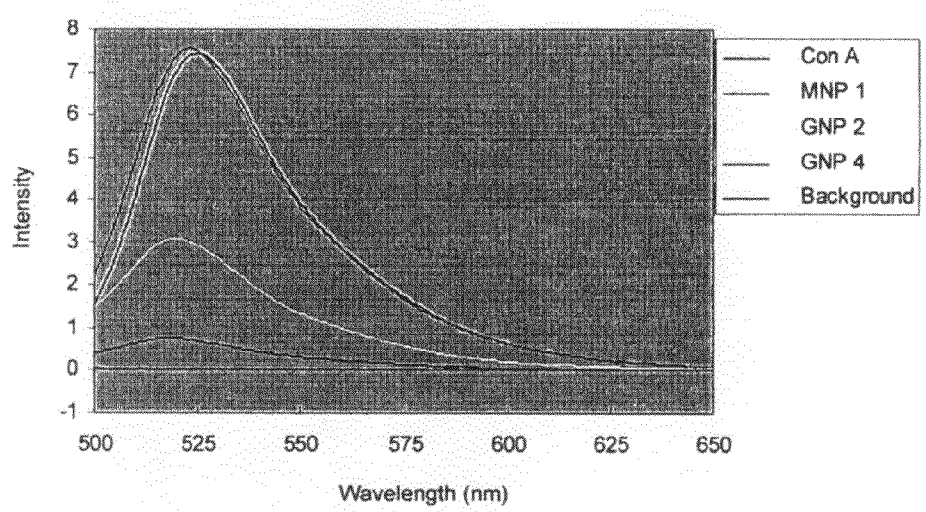
FIG. 8 is a graph comparing intensity to wavelength (nm) for Con A, MBP1, GNP 2, GNP 4, and the Background.
Figure 9:
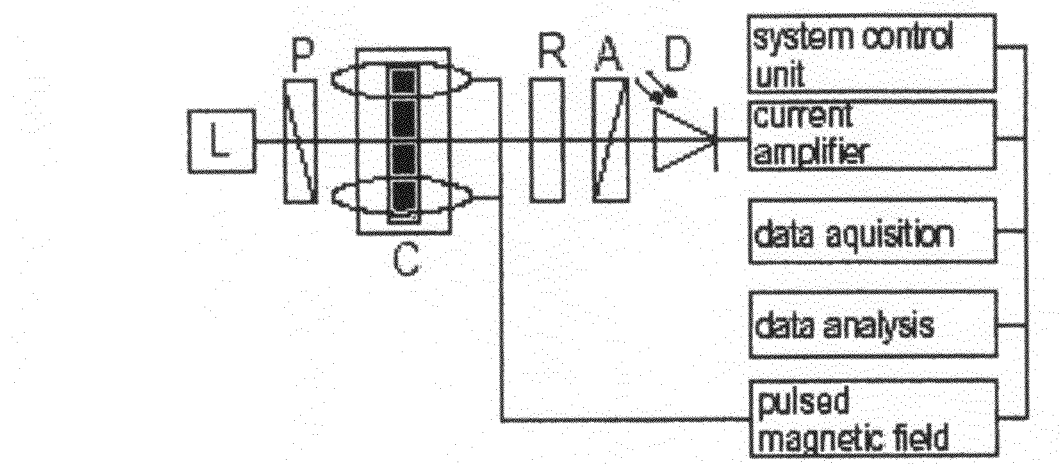
FIG. 9 is a schematic illustration of the measurement setup for the detection of the MO properties of nanoparticles in suspension (Faraday effect) (L: light source, P: polarizer, C: cell, R: retarding plate, A: analyzer, D: detector).

A second effect observed is the MO relaxation of the ferrofluid formed by the glyco-nanoparticles. In certain embodiments, the measurements of the magnetization relaxation are carried out in the magneto-optical method, as modified for transmission geometry (as shown in FIG. 8). Field-induced changes in the birefringence are capable of being detected because of the increased particle size due to aggregation. The use of plasmon-enhanced MO methods to monitor relaxation of the magnetization in ferrofluids is especially useful for real-time monitoring of biological binding events. FIG. 8 shows the measurement setup for the detection of the MO properties of nanoparticles in solution. (L: light source, P: polarizer, C: cell, R: retarding plate, A: analyzer, D: detector).

Selective Separation Using Magnetic Glyco-Nanoparticles

After the condition for the sensitive detection of Con A is established, the selective separation of Con A from a protein mixture using magnetic glyco-nanoparticles is conducted. Several proteins such as BSA, E. coli β-galactosidase and carbonic anhydrase, which are devoid of high affinity with α-mannosides, are mixed together with Con A. After incubating magnetic glyco-nanoparticles with the protein mixture, a magnet is applied to attract the glyco-nanoparticles to the wall of the container, followed by buffer washing to remove the residual protein solution. The amount of protein immobilized can be derived from the corresponding MO response without dissociating Con A from the nanoparticles. The purity of the protein immobilized is determined by gel electrophoresis after eluting Con A off the glyco-nanoparticles with mannoside 20, with the recovery yield calculated based on the amount of Con A retrieved.

Detection of Pathogens Using Magnetic Glyco-Nanoparticles

The pathogens such as E. coli are detected MNPs. Magnetic glyco-nanoparticles encapsulating mannoside 1-3, 7-9 and galactoside 4-6 are utilized. Multiple nanoparticles are attached to each cell, which leads to ready separation of cells from the media. With the large size differential between the E. coli bacteria (~μm) and glyco-nanoparticles, a strong MO response of the "glyco-nanoparticle-E. coli" complexes are observed, leading to high detection sensitivity, as discussed above.

It is to be noted that many types of bacteria may have surface adhesion proteins capable of recognizing the same oligosaccharide; an example of which is the cross recognition of mannose by *Salmonella enterica* and *E. coli*. The limitation of ligands with imperfect selectivities can be resolved through the usage of a glyco-nanoparticle array with different oligosaccharide ligands incorporated. Profiles of a pathogen can be created based on interactions with each member of the array allowing differentiation of various pathogens.

It is to be understood, therefore, that the present invention can be readily adapted to the detection of other pathogens besides *E. coli*. In other non-limiting examples, the magnetic glyco-nanoparticles are also useful as anti-infectious agents through multivalent inhibition of carbohydrate mediated microbe-host cell adhesion.

Magnetic Nanoparticles (MNPs) with Optimized Magneto-Optical Activity

Nanoparticles with multifold, core-shell structures, referred to as "nano-onions," are also useful since their multilayered structures exhibit unique magneto-optical effects usually observed in metallic multilayers of nanometer-scale thickness. A marked enhancement of the magneto-optical effect in composites is observed with spherical threefold nano-onions composed of Ag shells, $SiO_2$ intermediating shells, and magnetic cores of Fe, $CoFe_2O_4$. Thus, "nano-onion" MNPs are fabricated where the materials are chosen for enhanced magneto-optical activity. For example, the "nano-onions" can have a 3 nm Au core, a 1 nm Co layer, and a 2 nm Au coating, with all values corresponding to the radius manufactured using a sequential reverse micelle technique. The optimized MNPs are used in the fabrication of glyco-nanoparticles.

Evaluation of the Sensor Specificity and Sensitivity in *E. Coli* Detection

There is also provided herein, methods and articles for testing of environmental samples. Environmental samples typically pose unique challenges to optical detection methods due to their inherent complexity (i.e., the combination of its physical and chemical characteristics). In addition to sensor evaluation in the presence, of a complex media, the ionic strength, temperature, organic matter content, and pH can be varied, and relationships between changes in environmental conditions and sensor performance can then be established.

The detection of *E. coli* can be accomplished using a detection scheme similar to that for Con A, as described above. Magnetic glyco-nanoparticles encapsulating known *E. coli* ligands such as mannoside 1, 3 and galactoside 2 are utilized. Due to the relatively large size of a bacterial cell (~m), multiple nanoparticles are attached to each cell, which then are easily concentrated and separated from the media with a magnet. This is particularly advantageous in embodiments that involve the processing of environmental samples since pathogen concentrations can be low in these samples.

The *E. coli*/glyco-nanoparticle complexes can be attached to the magneto-optical sensor surface and their MO signals recorded. With the substantial size increase of the complexes as compared with nanoparticles alone, MO responses are significantly altered allowing sensitive detection of the bacteria. The amount of bacteria present can be correlated with the extent of MO signal changes, thus presenting a quantitative measure of pathogen level, which can be validated with the traditional cell culture based assay.

Magneto-Optical Response of Composite Materials Tailored by their Nanostructure.

Sub-nanometer modifications can be made in order to affect the magneto-optical response of the composite system in Co—Au nanostructures.

Figure 10:
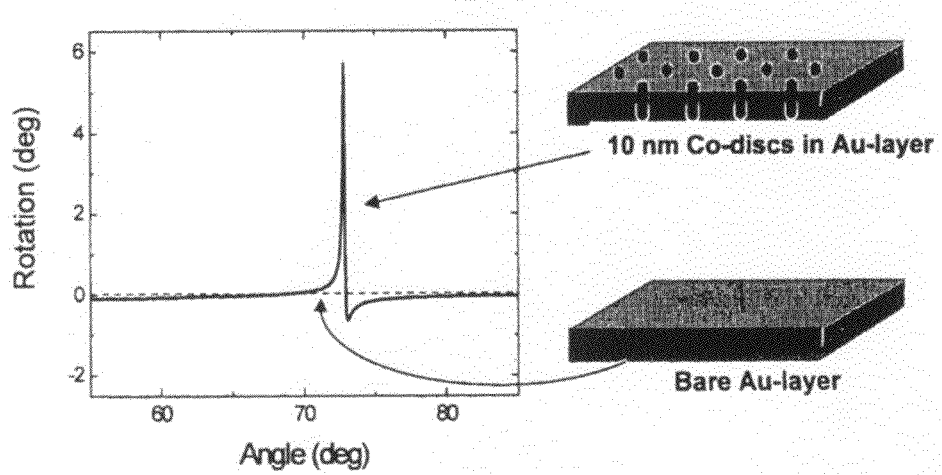
FIG. 10 is a schematic illustration of the magneto-optical Kerr rotation as a function of the incident angle in a Kretschmann reflection configuration and at fixed frequency (solid line: Co-discs embedded in Au-layer exhibiting sizable Kerr rotation, dashed line: bare Au-layer devoid of any observable Kerr rotation).

FIG. 10 is a schematic illustration of the magneto-optical Kerr rotation as a function of the incident angle in a Kretschmann reflection configuration and at fixed frequency (solid line: Co-discs embedded in Au-layer exhibiting sizable Kerr rotation, dashed line: bare Au-layer devoid of any observable Kerr rotation).

Figure 11:
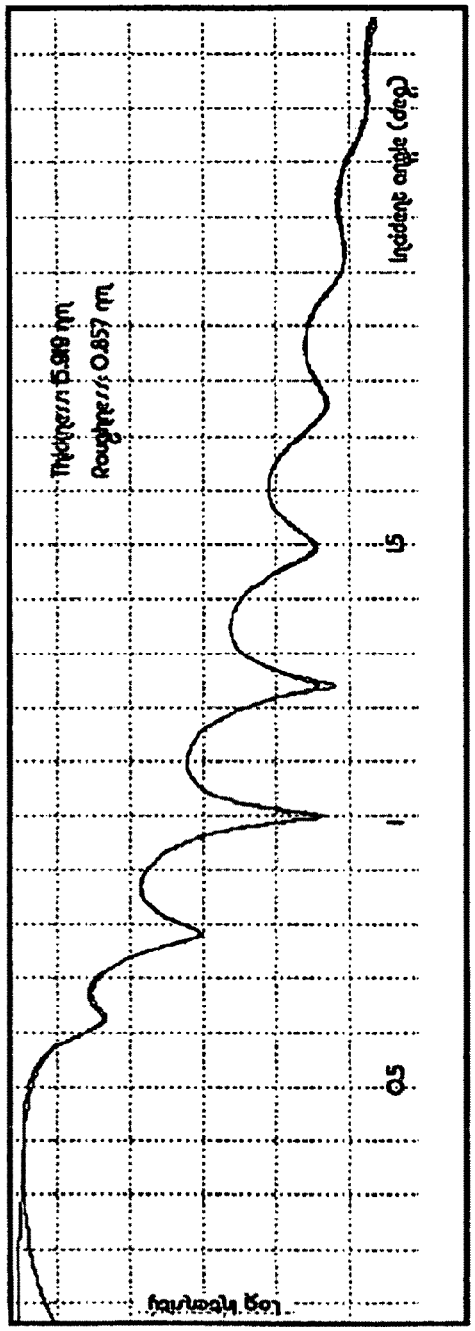
FIG. 11 shows the X-ray reflectometry scan for 16 nm Au film grown on glass and annealed at 300° C. for one hour.

In one non-limiting embodiment, the Au films were formed in an UHV chamber using thermal evaporation at room temperature; followed by thermal treatments to improve the morphology of the films. The structure of the films was characterized ex-situ using X-Ray Diffraction. FIG. 11 shows the X-ray reflectometry scan for 16 nm Au film grown on glass and annealed at 300° C. for one hour, indicating that the film is homogeneous in thickness and smoothness.

The thin film samples were mounted in the Toledo Heavy Ion Accelerator (THIA) and were implanted with 20 keV Co ions. Further optical characterization of the films was done in the Kretschmann configuration, consisting of a glass/metal/air interface, under total internal reflection. The complex dielectric function of the film is given by $\in = \in_1 + \in_2$. The real part of the dielectric constant is given by $\in = 1 - \omega_p^2/\omega^2$, where $\omega_p$ is the bulk plasmon frequency. The imaginary part of the dielectric constant describes the amount of energy absorbed by the metal. The reflectance of the light off of the metal film can be calculated using the following equation:

$$R = |r_{12} + r_{23}\exp(-2kd)/1 + r_{12}r_{23}\exp(-2kd)|^2$$

where $r_{nm}$, are the Fresnel reflection coefficients in the geometry considered (where the n and m subindices correspond to 1=air, 2=metal film and 3=glass), k is the absorption coefficient and d is the film thickness. In the example herein, a right-angle glass prism and matching index of refraction fluid at the prism-glass substrate interface were used. The measurements were carried out using HeNe laser with k=633 nm, polarization optics and the light detection were done using a photosensitive diode.

Figure 12:
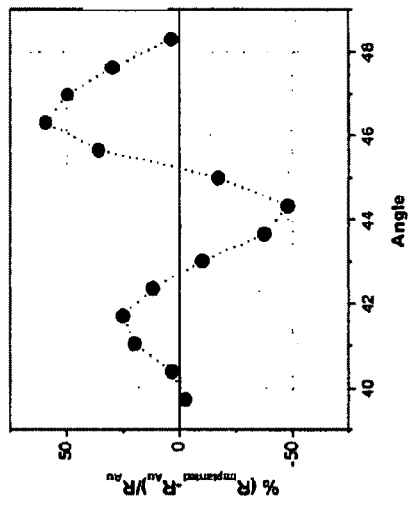
FIG. 12 shows the results obtained on the magneto-optical (MO) properties of nanoparticles implanted material as compared to a bare Au film.

FIG. 12 shows the results obtained on one typical implanted sample with respect to a bare Au film. The data is plotted as relative normalized reflectance (%) as function of incident angle. The implanted sample has a significant effect, in particular showing a marked minimum at 44 degrees. In FIG. 12, the relative reflectance (%) measured in the Kretschmann geometry on a Co—Au implanted nano-composite sample is shown as a function of incident angle. The wavelength of the HeNe light used is λ=633 nm.

The nano-structural modifications via ion-implantation applied to a noble metal thin film have substantial effect on its magneto-optical response. In particular, there is observed a 50 percent enhancement in SPR compared to the bare noble metal film.

Functionalization of Magnetic Nanoparticles (MNPs) with Organic Molecules: Loading Level Determination and Evaluation of Linker Length Effect on Immobilization Functionalization of MNPs with organic molecules was achieved by using a direct attachment approach. The amounts of rhodamine B loaded on MNPs were determined by UV-vis spectroscopy and the effect of linker length on immobilization was systematically evaluated. This method provides valuable quantitative information and is further applied to the determination of the amount of carbohydrate loaded on MNPs.

Preparation of the Magnetic Nanoparticles (MNPs)

Figure 13C:
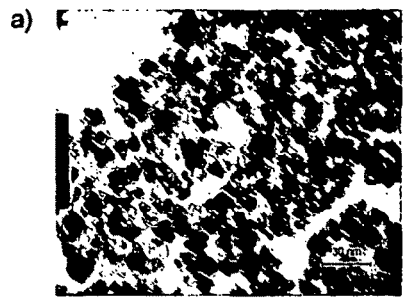
FIG. 13c shows XRD spectrum of uncoated MNPs.
Figure 13C:
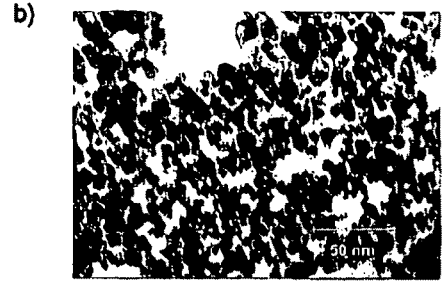
Figure 13C:
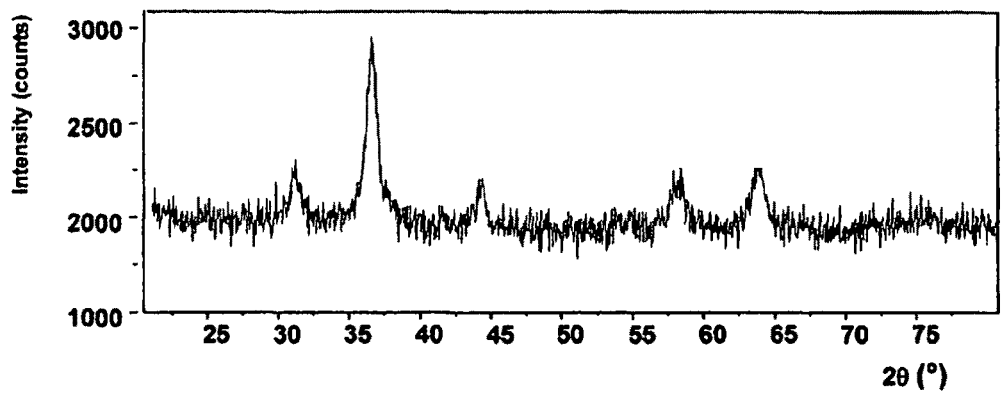
Figure 13D:
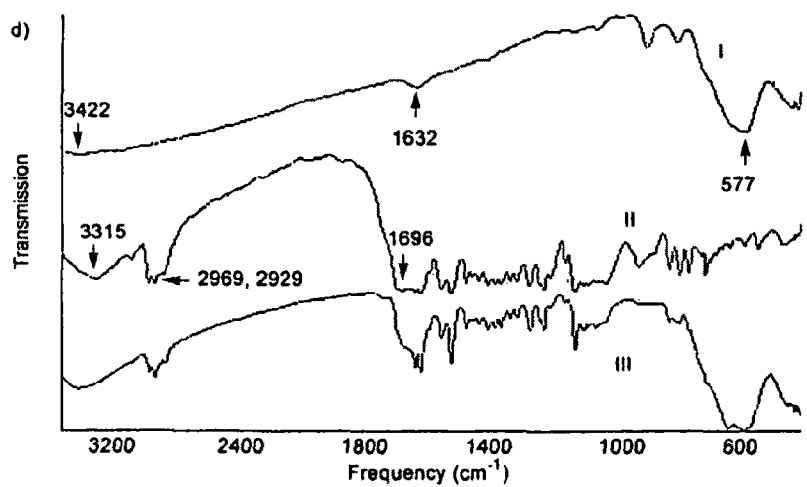
FIG. 13d shows IR spectra uncoated MNPs (trace I), rhodamine 2 (trace II), and rhodamine 2 coated MNPs (trace III).

The aqueous co-precipitation method without the use of any surfactants was used to obtain iron oxide nanoparticles. Several salts including $FeCl_3$, $Fe_2(SO_4)_3$ as sources for iron (III) and $FeCl_2$, $FeSO_4$ and $Fe(NO_3)_2$ for iron(II) were studied. NaOH and $NH_4OH$ were used as the base to adjust the final pH ranging from 9 to 13. Out of all the possible combinations of iron(III) and iron(II) salts screened, most reproducible results were obtained through the titration of $FeCl_3$ (0.67 M) and $FeSO_4$ (0.33 M) in 2M aqueous HCl solution with $NH_4OH$ until the final pH reached between 11 and 12. Under this condition, stable magnetic nanoparticle dispersion was consistently produced with a narrow size distribution around 10 nm as determined by TEM (see FIG. 13a). Powder XRD patterns confirmed the nanocrystalline structure of $Fe_3O_4$ particles (see FIG. 13c). IR spectra of these MNPs showed characteristic O—H stretching vibration at 3422 $cm^{-1}$, O—H deformed vibration at 1632 $cm^{-1}$ and Fe—O stretching vibration at 577 $cm^{-1}$ (FIG. 13d, trace I). The MNPs were stable above pH 7 and could be oxidized to γ-$Fe_2O_3$ by air.

Figure 14:
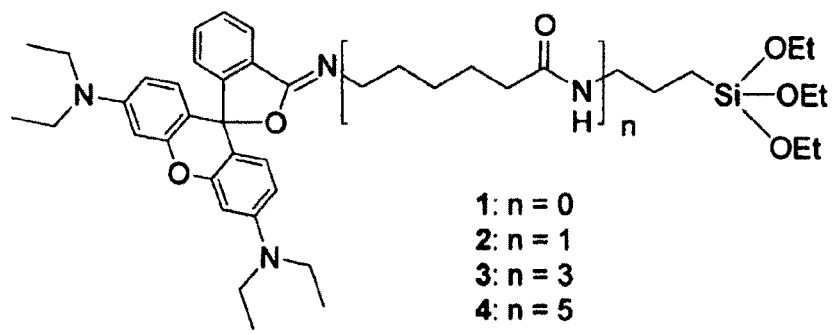
FIG. 14 shows rhodamine B APTES conjugated 1 to 4.
Figure 15:
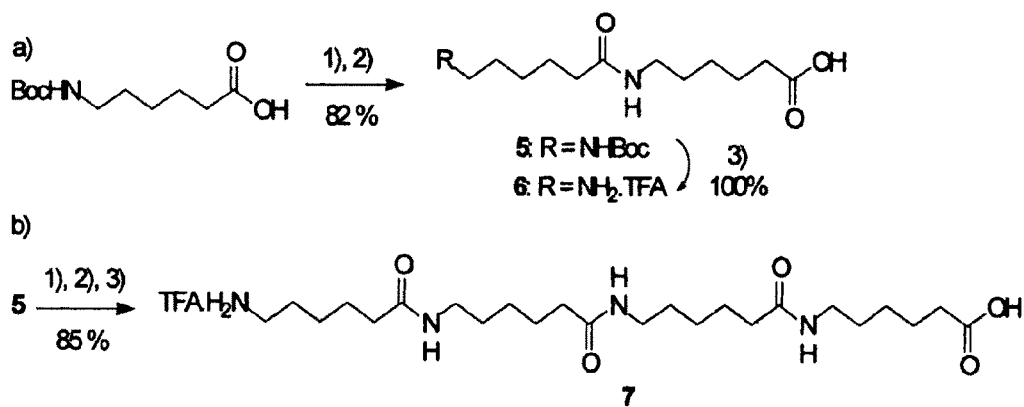

Syntheses of Rhodamine B Derivatives Containing APTES—(as Shown in FIGS. 14 and 15)

Rhodamine B was used to show the immobilization efficiencies due to its large size and its red-shifted absorbance. Instead of adopting the stepwise approach of coating MNP with aminopropyltriethoxy silane (APTES) first, rhodamine B was linked with APTES and the full conjugate was directly immobilized onto MNP in a single step. This allowed the quantitative determination of the maximum loading capacity of MNPs. Moreover, the coating of silica nanoparticles by APTES led to heterogeneous surface coverage due to hydrogen bonding of the APTES amino group, which was alleviated by first protecting the amino group of APTES prior to silanization. Derivatization of APTES first with rhodamine B prevented hydrogen bonding and led to more homogeneous distribution of ligands of MNP surfaces. Therefore, the rhodamine B APTES conjugates (shown as 1 to 4 in FIG. 14) with the linker length between the dye and alkoxysilane systematically varied.

In order to prepare the linker, N-Boc-6-aminocaproic acid was first converted to the N-hydroxysuccinimide (NHS) active ester using N-(3-dimethylaminopropyl)-N'-ethyl-carbodiimide hydrochloride (EDC), which was subsequently coupled to 6-aminocaproic acid (ACA) to form N-Boc diACA 5 (as shown in FIG. 15a). Treatment of the acid 5 (as shown in FIG. 14a) with trifluoroacetic acid (TFA) removed the N-Boc group, yielding amino acid diACA 6 (as shown in FIG. 15a) quantitatively. Amino acid tetraACA 7 (as shown in FIG. 15b) was synthesized in a similar fashion in 85% overall yield through coupling of acid 5 with diACA 6.

Figure 16:
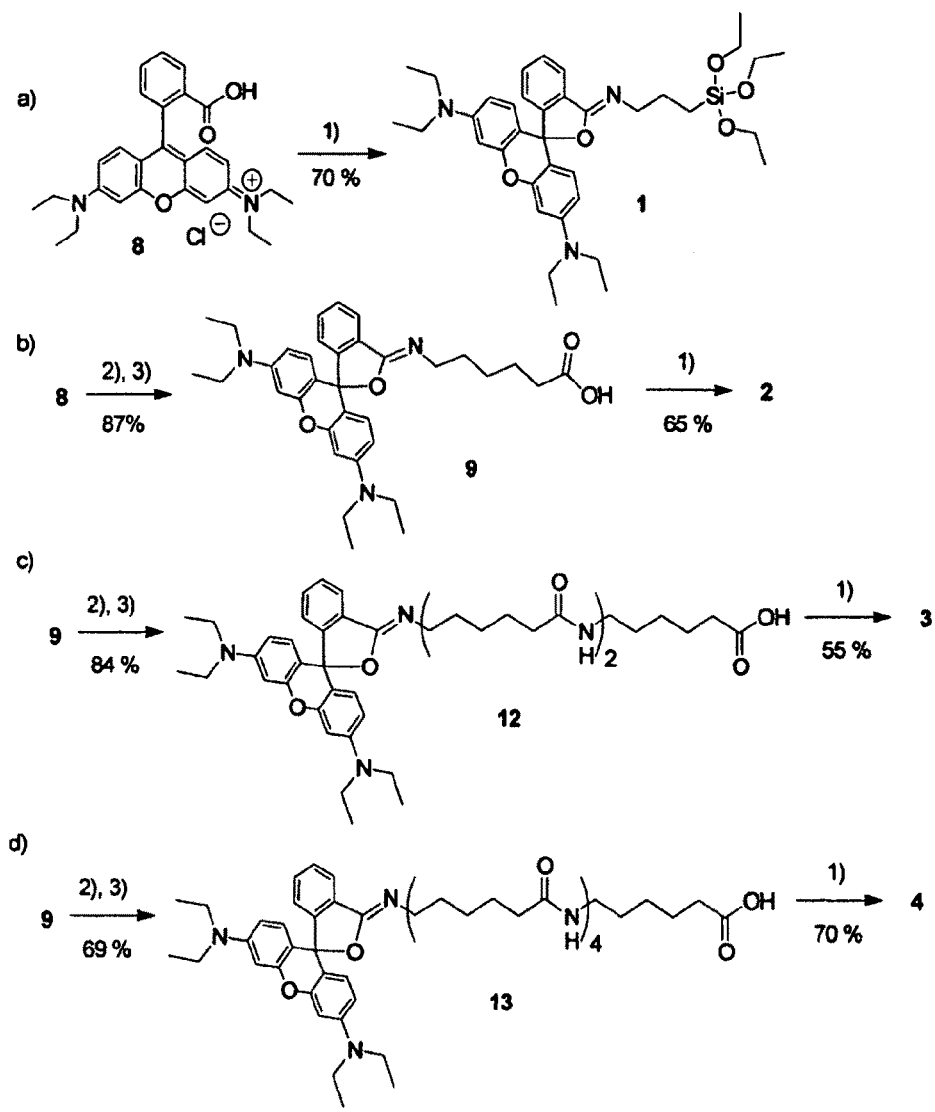
FIG. 16 shows—a) a method for preparing rhodamine B 8; b)—a method for preparing rhodamine B 2; c)—a method for preparing rhodamine B 3; and, d)—a method for preparing rhodamine B 4.

Rhodamine B 8 (as shown in FIG. 16a) was directly coupled with APTES forming compound 1 in 70% yield. In order to install the linker, rhodamine B 8 was first converted to NHS active ester, which was coupled to ACA producing acid 9 (as shown in FIG. 16b) in 87% yield. Amidation of 9 with APTES led to rhodamine B conjugate 2 with one ACA unit between rhodamine B and APTES (FIG. 16b). Repetition of this process with linkers 6 and 7 gave rhodamine B derivatives 3 and 4 (as shown in FIG. 16c,d) containing three and five ACA units between rhodamine B and APTES in good overall yields. The triethoxysilane moieties in compounds 1 to 4 are hydrolytically unstable. For all reactions involving triethoxysilanes, anhydrous reaction conditions were maintained to prevent hydrolysis. The desired products were purified by a quick silica gel column chromatography without any aqueous workup and they are stable at room temperature when stored under a nitrogen atmosphere.

Figure 17:
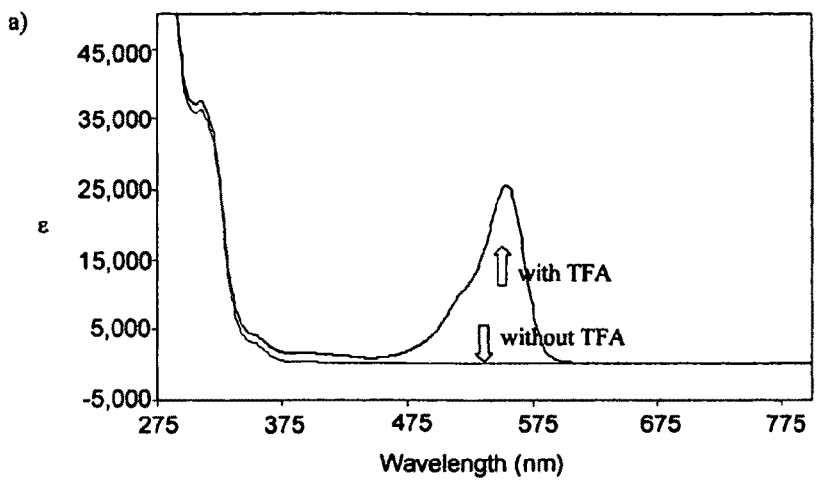
FIG. 17a shows the UV-vis spectra of rhodamine B 2 before and after addition of TFA.
FIG. 17b shows the Spiro isobenzofuran formation of rhodamine B.
Figure 17:
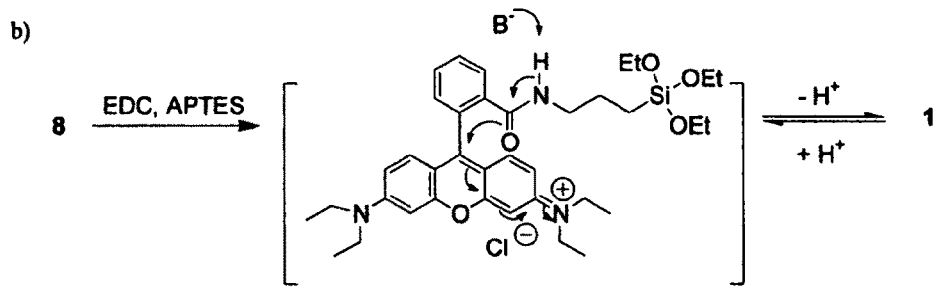

Due to its fully conjugated structure, rhodamine B 8 has the characteristic intense red color with the maximum absorbance at 554 nm. Interestingly, derivatives 1-4 are almost white, with their UV-vis spectra devoid of significant absorbance bands above 400 nm (see FIG. 17a). This was attributed to the loss of full conjugation due to a side reaction, i.e., cyclization of the amide onto the center ring of the xanthene moiety under the reaction condition to form the Spiro isobenzofuran (see FIG. 17b). This was supported by $^{13}$C-NMR, as a new peak around 97 ppm was observed corresponding to the quaternary spiral carbon. These rhodamine B derivatives fully regained the conjugation and color when TFA was added to the solution as evident from UV-vis spectra (see FIG. 17a).

Figure 18:
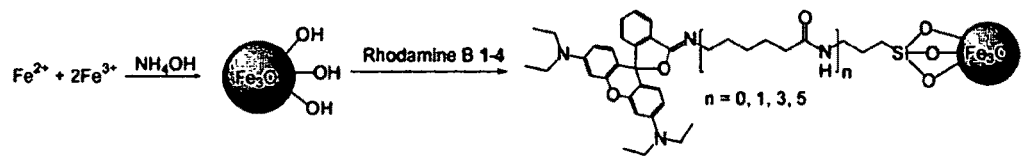
FIG. 18 shows a schematic illustration of a core-shell structure.

Immobilization of Rhodamine B Derivatives on MNPs and Surface Coverage Evaluations (as Shown in FIG. 18)

Various rhodamine B conjugates were immobilized onto MNPs through the silanization reaction to form a core-shell structure (see FIG. 18). Upon completion of the reaction, an external magnetic field was applied to the reaction mixture separating the nanoparticles from the supernatant. Multiple cycles of redispersion, magnetically induced precipitation on nanoparticles and washing were performed to remove all rhodamine B derivatives not covalently linked to the surface of nanoparticles.

Immobilization of rhodamine B derivatives on MNPs was confirmed by SEM-EDS and IR spectrum. SEM-EDS spectrum of immobilized MNPs indicated the presence of Fe, Si, C, N and O. IR spectrum of 2 showed NH stretching vibration at 3315 cm$^{-1}$, C—H vibration at 2969, 2929 cm$^{-1}$ and C=O stretching at 1696 cm$^{-1}$ (see FIG. 13d, trace II), while IR of rhodamine B 2 coated MNPs contained all the characteristic absorptions due to 2 along with additional bands resulting from MNPs (FIG. 13d, trace III). TEM images of rhodamine B coated MNPs demonstrated no significant morphology changes upon immobilization (FIG. 13b).

Figure 19:
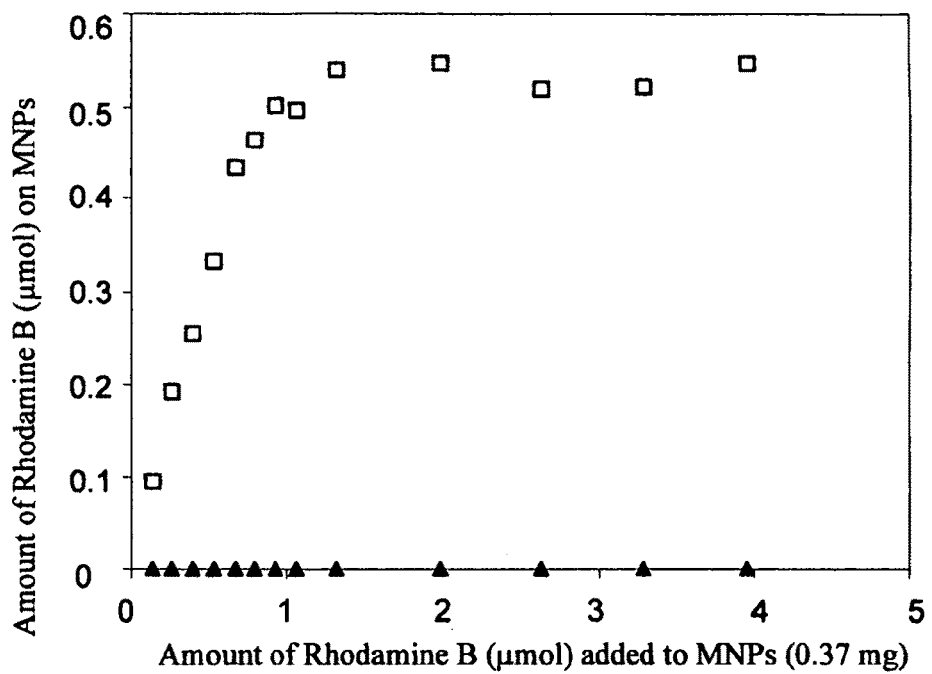
FIG. 19 is a graph showing the amount of rhodamine B immobilized on MNPs (0.37 mg) as calculated from subtracting the amount of un-immobilized dye from the total amount added for the silanization reaction. ($\square$ for compound 2, $\blacktriangle$ for rhodamine B 8).

To determine the maximum level of rhodamine B that could be loaded on MNP surface, varying amounts of the rhodamine B APTES conjugates were added to a fixed quantity of MNP. The amount of rhodamine B attached onto MNPs was first determined indirectly by subtracting the amount of dye left in the solution after the silanization reaction from the amount added. The dye concentrations were calculated from its absorbance at 554 nm after first establishing a standard calibration curve in the presence of TFA. The amount of compound immobilized onto MNP linearly increased at low concentrations of added rhodamine B until surface saturation of nanoparticles was reached as indicated by the plateau in absorbance (see FIG. 19). Interestingly, maximum loading levels around $1.5 \times 10^{-3}$ mol/g of MNPs were achieved for rhodamine B derivatives 1 to 3 (as shown in FIG. 14) containing 0 to 3 ACA linker units, while for rhodamine B 4, slightly less compound ($1.1 \times 10^{-3}$ mol/g of MNPs) was attached, as shown in Table 1 below. These results indicated that linker length does not play a significant role in determining immobilization efficiencies, which alleviates concerns of possible steric effects of immobilized molecules on MNPs.

TABLE 1

Maximum loading levels of rhodamine B derivatives 1 to 4 (as shown in FIG. 14) on MNPs.

| Rhodamine B derivative | Maximum Loading Level (mol/g) | Minimum Amount (mol/g) Needed for Surface Saturation |
|---|---|---|
| 1 | $1.44 \times 10^{-3}$ | $2.79 \times 10^{-3}$ |
| 2 | $1.50 \times 10^{-3}$ | $2.78 \times 10^{-3}$ |
| 3 | $1.53 \times 10^{-3}$ | $2.13 \times 10^{-3}$ |
| 4 | $1.11 \times 10^{-3}$ | $1.74 \times 10^{-3}$ |

The loading levels obtained are approximately two orders of magnitudes higher than those previously determined by a colorimetric assay of APTES coated rhombic MNPs. The discrepancy can be explained by the smaller size and the spherical shape of our MNPs and the direct MNP derivatization method used instead of the stepwise modification approach. In all, approximately 60% of the rhodamine B derivatives added were immobilized on nanoparticles before reaching the saturation point with the remaining compounds presumably consumed by the competitive hydrolysis reaction.

In order to exclude the possibility of nonspecific binding, rhodamine B 8 devoid of the trialkoxysilane moiety was incubated with MNPs under identical conditions for silanization, and the amount of rhodamine B 8 absorbed on the MNP's surface was determined by UV-vis measurement in the same manner as described above. Even though rhodamine B 8 contains a negatively charged carboxylic acid moiety, its binding with the MNP was minimal (see FIG. 19) under our experimental conditions.

Figure 20:
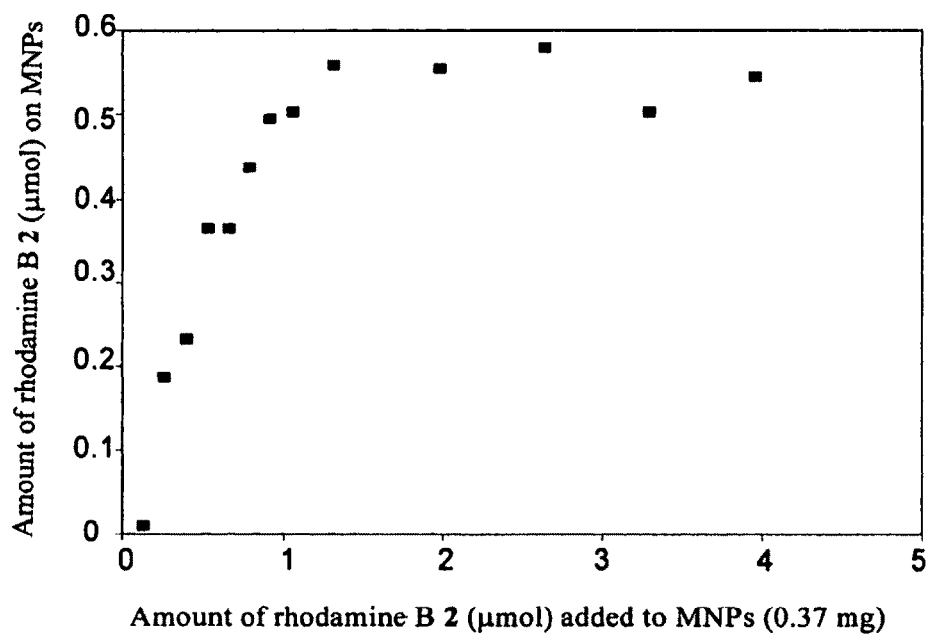
FIG. 20 is a graph showing the amount of rhodamine B 2 immobilized on MNPs (0.37 mg) as directly determined from UV-vis ($\lambda_{max}$=554 nm, $\in$=25,612) after dissolving the coated MNPs with TFA.

While rhodamine B derivatives 1 to 4 quickly regained its characteristic red color in solution within a few seconds of TFA (20 µl/mg) addition (see FIG. 17a), UV-vis spectra of the MNP coated with rhodamine B derivatives were found devoid of absorbance above 400 nm when the same amount of TFA was applied. To confirm that the unrecovered dyes were indeed present on the MNPs, we dissolved the MNPs core by adding a large amount of acid. Under the high acidic condition, MNPs disintegrate releasing free rhodamine B into the solution. Upon addition of excess TFA (200 µl/mg) to MNPs containing rhodamine B 2, the red color fully recovered after one day. UV-vis measurement of the amount of rhodamine B released from MNPs (see FIG. 20) matched that determined using the indirect method (FIG. 18). The reason for the much slower re-generation of fully conjugated form of rhodamine B dye on MNP is not clearly understood.

Figure 21:
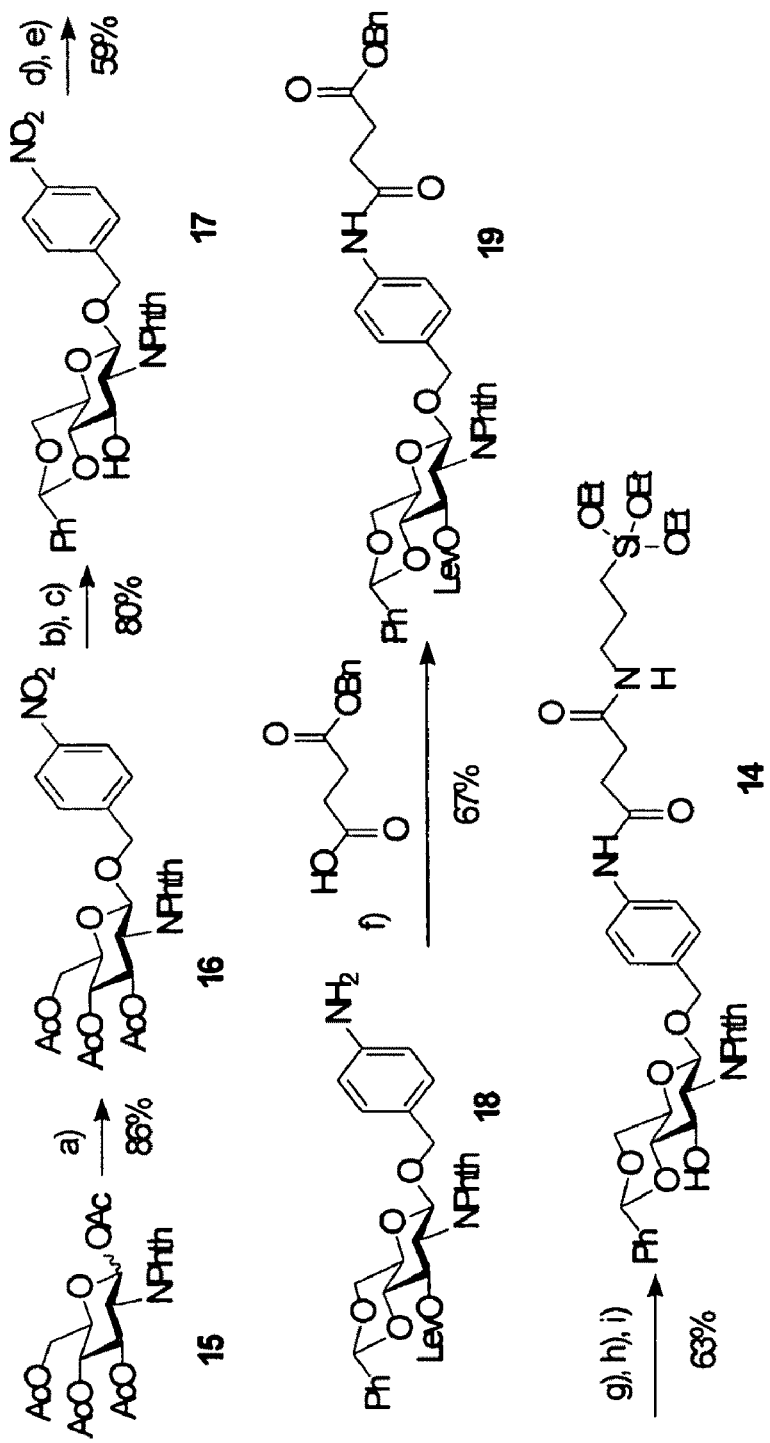
FIG. 21 shows the synthesis of a glucosamine derivative 14.

Rhodamine family dyes are popular fluorophores, which have been attached to nanoparticles for cellular imaging and immunoassays. Our results indicate that for quantitative studies by UV-vis or fluorescence using rhodamine on nanoparticles, the formation of the Spiro isobenzofuran and slow regeneration of conjugation, which can dramatically reduce its absorbance in the visible region, must be taken into consideration Synthesis of Carbohydrate Modified APTES—(as Shown in FIG. 21)

Carbohydrates play important roles in many biological processes. Glyco-nanoparticles, i.e., nanoparticles with carbohydrates immobilized on the exterior, are emerging as promising tools for glycobiological studies. It is known that the density of carbohydrates on a surface is crucial for their biological functions. As a model for our glyco-nanoparticle studies, we chose to immobilize glucosamine derivative 14 (as shown in FIG. 21) because of important biological properties of glucosamine derivatives. The synthesis of 14 started from 1,3,4,6-tetra-O-acetyl 2-deoxy-2-N-phthalimido-D-glucopyranoside 15, which was efficiently converted to β-nitrobenzyl glycoside 16 using $SnCl_4$ as the Lewis acid catalyst (see FIG. 21). The three acetates in 16 were removed by the treatment with NaOMe at $-10°$ C., followed by benzylidene protection leading to acetal 17 in 80% yield for the two steps. Levulinoyl protection and selective reduction of the nitro moiety produced amine 18 (59% yield). Reaction of compound 18 with succinic anhydride using N,N-dimethylamino pyridine (DMAP) as the nucleophilic catalyst even at reflux conditions did not produce any desired amide due to the low nucleophilicity of anilinilic nitrogen in 18. Amidation of compound 18 by O-benzylsuccinate with EDC/DMAP failed as well. Finally, amide 19 was produced in 67% yield using BOP reagent/N,N-diisopropylethyl amine at room temperature for 48 hours. Deprotection of the levulinoyl group and subsequent controlled hydrogenation to generate the carboxylic acid followed by amidation of APTES afforded target compound 14 in 63% yield. The compound 14 is stable at room temperature when stored under a nitrogen atmosphere.

Immobilization of Sugar Modified APTES on MNPs and Surface Coverage Evaluations

Figure 22:
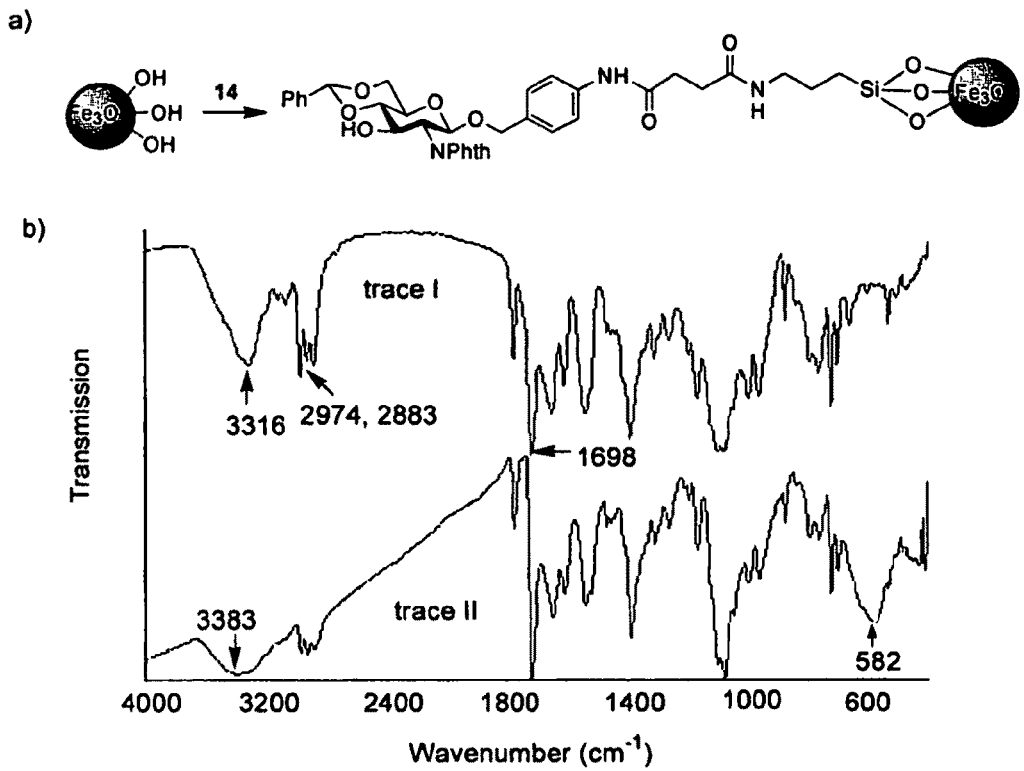
FIG. 22a shows a schematic illustration of the attachment of glucosamine 14 to MNPs through the silanization reaction.

In order to determine the maximum amount of glucosamine derivative 14 that can be loaded on MNPs, increasing concentrations of 14 were added to a fixed quantity of uncoated MNPs. Upon completion of the silanization reaction (see FIG. 22a), an external magnetic field was applied to the reaction mixture separating the nanoparticles from the supernatant, followed by multiple cycles of redispersion, magnetically induced precipitation of MNPs and washing. TEM images of the resulting glyco-nanoparticles indicated no significant morphology changes. SEM-EDS demonstrated the presence of N, C, Fe, Si and O on MNPs. IR spectrum of 14 showed characteristic broad absorption at 3316 $cm^{-1}$ due to N—H and O—H stretching vibrations, C—H stretching vibration at 2974, 2883 $cm^{-1}$ and C=O stretching at 1698 $cm^{-1}$ (see FIG. 22b, trace II). Glyco-nanoparticles showed all IR absorptions due to 14 along with characteristic O—H stretching vibration at 3383 $cm^{-1}$ and Fe—O stretching vibration at 582 $cm^{-1}$ from MNPs (see FIG. 22bb, trace I), thus confirming the immobilization of 14 on MNPs.

Figure 23:
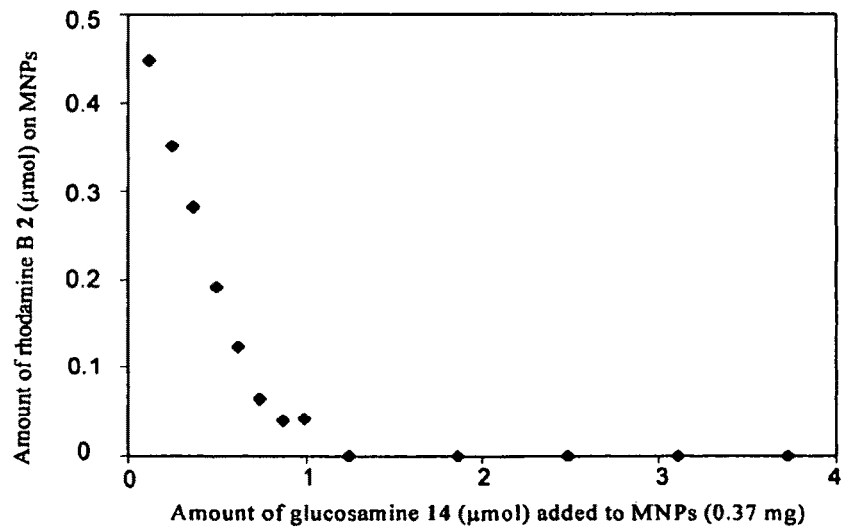
FIG. 23 is a graph showing that, with increasing amounts of glucosamine 14 used for silanization reaction, the amounts of rhodamine B 2 that could be attached on glyco-nanoparticles decreased.

Because glucosamine 14 lacks chromophores absorbing in the visible region, it is difficult to directly determine its loading level on glyco-nanoparticles by UV-vis spectroscopy due to interference from the light scattered by MNPs. In order to quantify carbohydrates on glyco-nanoparticles, a fixed amount of rhodamine B 2 was added to glyco-nanoparticles. For glyco-nanoparticles prepared with increasing concentrations of glucosamine 14, the additional amount of rhodamine B 2 that could be immobilized onto these nanoparticles decreased, which became zero after 1.0 μmol of glucosamine 14 was added to MNPs (0.37 mg) (see FIG. 23). This indicated that the maximum loading level of glucosamine 14 on MNPs was $1.6×10^{-3}$ mol/g assuming 60% of 14 added was immobilized. The maximum amount of 14 that can be attached on MNPs is similar to that of rhodamine B, thus confirming that the silanization reaction is not influenced by the identity of the molecules to be loaded. Furthermore, the presence of a free hydroxyl group in glucosamine 14 does not interfere with loading. This signifies that the silanization approach may be used as a general method to functionalize MNPs.

Materials and Methods

General: $^1$H-NMR (400 MHz or 600 MHz) and $^{13}$C-NMR (100 MHz or 150 MHz) spectra were recorded at room temperature. Chemical shift (δ) values are given in ppm. Mass spectra were recorded on an ESQUIRE LC-MS using ESI technique to introduce the sample. IR spectra were recorded as KBr pellet forms using FTIR Perkin Elmer Spectrum GX with ATR capabilities. UV-vis spectra were recorded on a Beckman DU-50 spectrophotometer. Air- and moisture-sensitive liquids and solutions were transferred via syringes. Organic solutions were concentrated by rotary evaporation below 40° C. at ca. 25 Torr. Flash column chromatography was performed employing 230-400 mesh silica gels. Thin-layer chromatography was performed using glass plates pre-coated to a depth of 0.25 mm with 230-400 mesh silica gel impregnated with a fluorescent indicator (254 nm). TLC plates were visualized with UV light and/or by staining either with a yellow stain (containing $Ce(NH_4)_2(NO_3)_6$ (0.5 g) and $(NH_4)_6Mo_7O_{24}.4H_2O$ (24.0 g) in 6% $H_2SO_4$ (500 mL) or a pink stain (containing $KMnO_4$ (3 g), $K_2CO_3$ (20 g), 5% aq. NaOH (5 mL) in 300 mL $H_2O$). The nanoparticles were characterized on carbon coated Formvar support film 300 mesh copper grids with a TEM microscope (Philips, CM10 Mawah, N.J., software Image Pro Plus 6.0). For TEM sample preparation, MNPs were suspended in ethanol using sonication for 30 minutes and then drop-cast on a TEM grid. SEM-EDS spectra were obtained using JEOL JSM 6100 SEM with Link/eXL Energy Dispersive X-ray Spectrometer. Powder XRD spectrum was obtained using PAnalytical X'pert Pro MPD with CuKα radiation.

Preparation of $Fe_3O_4$ Nanoparticles

For MNP synthesis, 1M ferric chloride and 1M ferrous sulfate solutions were prepared by dissolving ferric chloride hexahydrate ($FeCl_3.6H_2O$>99%, 27.1 g) and ferrous sulfate heptahydrate ($FeSO_4.7H_2O$>99%, 27.8 g) in 2M HCl (100 mL), respectively. Degassed and deionized water was used to prepare all the solutions. To prepare $Fe_3O_4$ nanoparticles, 1M aqueous $FeCl_3$ (10 mL) solution was mixed with 1M aqueous $FeSO_4$ (5 mL) solution in a flask under a nitrogen atmosphere. Ammonium hydroxide solution (~30 mL) was slowly added with vigorous stirring until a pH between 11 and 12 was reached. Vigorous stirring was continued for another 30 minutes. The solution color could be seen to alter from orange to black, leading to black $Fe_3O_4$ nanoparticles. The MNPs were isolated by applying a permanent external magnet (Lifesep® 50SX magnetic separator). The supernatant was discarded by decantation. Deionized and degassed water was then added to wash the particles thoroughly and was repeated for 5 times to remove excess ions and salts. Finally, particles were washed with ethanol two times and stored as dispersion in ethanol.

Preparation of MNPs Coated with Rhodamine B Derivatives and Loading Evaluations

To vials each containing MNPs (0.37 mg) were added respectively 0.1, 0.2, 0.3, 0.4, 0.5, 0.6, 0.7, 0.8, 1, 1.5, 2, 2.5 and 3 mg of rhodamine B derivative in absolute ethanol (2 mL) under nitrogen. The vial sets were mechanically shaken for 24 hrs. Rhodamine B coated MNPs were isolated by positioning a permanent external magnet (Lifesep® 50SX magnetic separator) on the side of the vial. The supernatant was carefully collected by a pipette, the particles were washed with ethanol and redispersed by shaking. Several cycles of magnetically induced precipitation washing and redispersion were performed. All ethanol solutions were combined and diluted to a fixed volume, to which trifluoroacetic acid (TFA, 10 μL) was added. UV-vis spectrum of the solution was measured, from which the amount of unattached dye was calculated based on its absorbance at 554 nm. The amount of dye loaded on MNPs was obtained by subtracting the amount of unattached dye from that added for the silanization reaction.

Preparation of MNPs Coated with Glucosamine 14 and Loading Evaluation of the Resulting Glyco-Nanoparticles To vials each containing MNPs (0.37 mg) were added respectively 0.1, 0.2, 0.3, 0.4, 0.5, 0.6, 0.7, 0.8, 1, 1.5, 2, 2.5 and 3 mg of glucosamine 14 in absolute ethanol (2 mL) under nitrogen. The vial sets were mechanically shaken for 24 hrs. The glyco-nanoparticles were isolated by positioning a permanent external magnet (Lifesep® 50SX magnetic separator) on the side of the vial. The supernatant was carefully removed by pipette and particles were washed several times with ethanol. Subsequently, rhodamine B derivative 2 (1 mg) in absolute ethanol (2 mL) was added to nanoparticles in each vial. The vial sets were mechanically shaken for 24 hours under nitrogen, after which nanoparticles were isolated by positioning a permanent external magnet on the side of the vial. The supernatant was carefully collected by a pipette, and the particles were washed with ethanol. All solutions were combined and diluted to a fixed volume, to which TFA (10 μL) was added. UV-vis spectra of the solutions were recorded from which the amount of unattached dye was measured based on its absorbance at 554 nm ($\in$=25,612). The amount of dye immobilized an MNPs was calculated by subtracting the amount of unattached dye from its amount added. The amount of glucosamine 14 attached on MNPs was assumed to be 60% of the amount of 14 added for the silanization reaction. The sum of glucosamine 14 and rhodamine B 2 immobilized on MNPs equals 1.6 mmol/g, which is the maximum quantity of compounds that can be loaded on MNPs.

Rhodamine B APTES Conjugate (1). To a mixture of rhodamine B 8 (500 mg, 1.04 mmol) and APTES (254 mg, 1.15 mmol) in dry $CH_2Cl_2$ (DCM) (20 mL) EDC (300 mg, 1.57 mmol) was added. The reaction mixture was stirred under a $N_2$ atmosphere at room temperature overnight. Solvent was evaporated and the product was purified by flash chromatography (15% methanol in DCM) in 70% yield. $^1$H-NMR (400 MHz, $CDCl_3$) δ 7.88-7.90 (m, 1H), 7.36-7.42 (m, 2H), 7.02-7.04 (m, 1H), 6.46 (s, 1H), 6.44 (s, 1H), 6.37 (d, 2H, J=2.4 Hz), 6.26 (dd, 2H, J=2.4, 8.8 Hz), 3.64 (q, 6H, J=7.2 Hz), 3.32 (q, 8H, J=7.2 Hz), 3.09-3.14 (t, 2H, J=7.2 Hz), 1.31-1.35 (m, 2H), 1.13-1.17 (t, 12H, J=7.2 Hz), 1.11 (t, 9H, J=7.2 Hz), 0.40-0.46 (m, 2H); $^{13}$C-NMR (100 MHz, $CDCl_3$) δ 168.0, 153.9, 153.2, 148.6, 132.1, 131.3, 129.0, 127.8, 123.7, 122.6, 107.9, 105.9, 97.6, 64.8, 58.1, 44.3, 43.3, 21.7, 18.2, 12.6, 8.2; ESI-MS: m/z: calcd for $C_{37}H_{52}N_3O_5Si$: 646.4. found: 646.5 $[M+H]^+$ N-Boc-diACA (5). To a mixture of N-Boc-6-aminocaproic acid (2 g, 8.65 mmol) and N-hydroxysuccinimide (0.995 g, 8.65 mmol) in dry DCM (75 mL), N-(3-dimethylaminopropyl)-N'-ethyl-carbodiimide hydrochloride (EDC) (2.49 g, 13 mmol) was added. The reaction mixture was stirred under a $N_2$ atmosphere at room temperature overnight. The reaction mass was washed with saturated brine and organic layer was dried over anhydrous $Na_2SO_4$. Solvent was evaporated to give succinimidyl activated ester as a white solid (2.56 g, 90% yield). $^1$H NMR (400 MHz, $CDCl_3$) δ 4.65 (bs, 1H), 3.00-3.10 (m, 2H), 2.80 (s, 4H), 2.57 (t, 2H, J=7.2 Hz), 1.70-1.74 (m, 2H), 1.37-1.51 (m, 13H); $^{13}$C NMR (100 MHz, $CDCl_3$) δ 169.4, 168.7, 156.2, 79.2, 40.4, 31.0, 29.7, 28.6, 26.1, 25.8, 24.4; ESI-MS: m/z: calcd for $C_{15}H_{24}N_2O_6Na$: 351.1. found: 351.1 $[M+Na]^+$.

To a mixture of succinimidyl activated ester (1 g, 3.05 mmol) and 6-aminocaproic acid (0.4 g, 3.05 mmol) in dry DMF (30 mL), triethylamine (1.3 mL, 9.15 mmol) was added. The reaction mixture was stirred under a $N_2$ atmosphere at room temperature for overnight. DMF was removed under reduced pressure and diluted with ethyl acetate. The solution was washed with aqueous 1N HCl solution. Organic layer was dried over anhydrous $Na_2SO_4$. Solvent was evaporated, and the product 5 was obtained by recrystallization using 1:1 ethyl acetate:hexanes (0.97 g, 92% yield). $^1$H NMR (400 MHz, $CD_3OD$) δ 3.15 (t, 2H, J=7.2 Hz), 3.01 (t, 2H, J=7.2 Hz), 2.29 (t, 2H, J=7.2 Hz), 2.16 (t, 2H, J=7.2 Hz), 1.57-1.64 (m, 4H), 1.27-1.51 (m, 17H); $^{13}$C NMR (100 MHz, $CD_3OD$) 176.3, 174.9, 157.4, 78.6, 40.0, 38.9, 35.8, 33.6, 29.5, 28.9, 27.6, 26.3, 25.6, 24.5; ESI-MS: m/z: calcd for $C_{17}H_{32}N_2O_5Na$: 367.2. found: 367.3 $[M+Na]^+$ DiACA (6). Compound 5 (1 g) was dissolved in 1:1 TFA/water (10 mL) and stirred at room temperature for 2 hours. Solvents were removed under reduced pressure to give oily product 6 (100% yield). Traces of water from the product were removed by co-evaporation with toluene. $^1$H-NMR (600 MHz, $CD_3OD$) δ 3.12-3.16 (m, 2H), 2.92 (t, 2H, J=7.2 Hz), 2.26-2.31 (m, 2H), 2.19 (t, 2H, J=7.2 Hz), 1.56-1.69 (m, 6H), 1.45-1.52 (m, 2H), 1.27-1.41 (m, 4H); $^{13}$C-NMR (100 MHz, $CD_3OD$) δ175.5, 175.8, 175.7, 175.6, 52.0, 40.5, 40.1, 36.6, 34.8, 34.6, 30.0, 29.9, 28.1, 27.4, 27.3, 26.8, 26.3, 25.6, 25.5; ESI-MS: calcd for $C_{12}H_{25}N_2O_3Na$: 268.2. found: 268.8 $[M+H+Na]^+$.

TetraACA (7). To a mixture of N-Boc-diACA compound 5 (1.0 g, 2.9 mmol) and N-hydroxysuccinimide (368 mg, 3.2 mmol) in dry DCM (50 mL) EDC (834 mg, 4.4 mmol) was added. The reaction mixture was stirred under a $N_2$ atmosphere at room temperature overnight. The reaction mass was washed with saturated brine and organic layer was dried over anhydrous $Na_2SO_4$. Solvent was evaporated to give succinimidyl activated ester as a white solid (1.18 g, 92% yield). $^1$H-NMR (600 MHz, $CDCl_3$) δ 5.77 (s, 1H), 4.57 (s, 1H), 3.21-3.25 (m, 2H), 3.05-3.09 (m, 2H), 2.82, 2.83 (2s, 4H), 2.60 (t, 2H, J=7.2 Hz), 2.14 (t, 2H, J=7.2 Hz), 1.72-1.77 (m, 2H), 1.58-1.64 (m, 2H), 1.48-1.52 (m, 2H), 1.39-1.47 (m, 11H), 1.27-1.32 (m, 2H); $^{13}$C-NMR (100 MHz, $CDCl_3$) δ 173.2, 169.5, 168.7, 79.2, 40.6, 39.1, 36.6, 31.0, 29.9, 29.1, 28.6, 25.9, 25.8, 25.5, 25.4. To a mixture of the succinimidyl activated ester (500 mg, 1.13 mmol) and diACA 6 (406 mg, 1.13 mmol) in dry DMF (15 mL), triethylamine (0.64 mL, 4.5 mmol) was added. The reaction mixture was stirred under a $N_2$ atmosphere at room temperature overnight. Reaction solvents were removed under reduced pressure and then diluted with ethyl acetate. The solution was washed with 1N aqueous HCl solution. The organic layer was dried over anhydrous $Na_2SO_4$. Solvent was evaporated, and the N-Boc protected tetraACA was obtained by recrystallization using 1:1 ethyl acetate:hexanes (595 mg, 92% yield). $^1$H-NMR (400 MHz, $CD_3OD$) δ 3.12-3.16 (m, 6H), 2.99-3.13 (m, 2H), 2.12-2.17 (m, 6H), 1.26-1.65 (m, 35H); $^{13}$C-NMR (100 MHz, $CD_3OD$) δ 176.2, 174.9, 174.8, 170.658, 157.356, 40.0, 39.0, 38.9, 35.9, 35.9, 35.8, 33.6, 30.3, 29.5, 28.9, 28.7, 27.6, 26.4, 26.3, 25.8, 25.6, 25.5, 25.3, 24.5, 24.2; ESI-MS: m/z: calcd for $C_{29}H_{53}N_4O_7$: 569.4. found: 569.2 $[M-H]^-$. N-Boc protected tetraACA (500 mg) was dissolved in 1:1 TFA/water (5 mL) and stirred at room temperature for 2 hours. Solvents were removed under reduced pressure to give oily product tetraACA 7 (100% yield). Traces of water from the product were removed by co-evaporation with toluene. $^1$H-NMR (400

MHz, CD$_3$OD) δ 3.12-3.18 (m, 6H), 2.86-2.93 (m, 2H), 2.26-3.32 (m, 2H), 2.14-2.22 (m, 6H), 1.58-1.70 (m, 10H), 1.46-1.54 (m, 6H), 1.30-1.43 (m, 8H); $^{13}$C-NMR (100 MHz, CD$_3$OD) δ176.3, 174.9, 174.6, 39.3, 39.0, 35.8, 35.4, 33.6, 28.9, 27.1, 26.3, 25.7, 25.5, 25.1, 24.5 ESI-MS: m/z: calcd for C$_{24}$H$_{45}$N$_4$O$_5$: 469.3. found: 469.2 [M−H]$^-$.

Rhodamine B ACA Conjugate (9). To a mixture of rhodamine B 8 (2 g, 4.18 mmol) and N-hydroxysuccinimide (0.528 g, 4.6 mmol) in dry DCM (100 mL) EDC (1.21 g, 6.27 mmol) was added. The reaction mixture was stirred under N$_2$ atmosphere at room temperature overnight. Solvent was evaporated and the succinimidyl activated ester was purified by flash chromatography (1:10 methanol/DCM) in 90% yield. $^1$H-NMR (600 MHz, CD$_3$OD) δ 8.42 (d, 1H, J=7.8 Hz), 8.00 (t, 1H, J=7.8 Hz), 7.90 (t, 1H, J=7.8 Hz), 7.58 (d, 1H, J=7.8 Hz), 7.14 (s, 1H), 7.12 (s, 1H), 7.03 (dd, 2H, J=6.0, 9.0 Hz), 6.95 (d, 2H, J=1.8 Hz), 3.66 (q, 8H, J=7.2 Hz), 2.69 (s, 4H), 1.29 (t, 12H, J=7.2 Hz); $^{13}$C NMR (100 MHz, CDCl$_3$) δ 168.9, 160.9, 157.9, 155.9, 155.8, 135.1, 134.6, 131.9, 131.2, 130.9, 125.5, 114.6, 113.6, 96.6, 77.1, 50.6, 25.8, 12.8; ESI-MS: m/z: calcd for C$_{32}$H$_{34}$N$_3$O$_5$: 540.3. found: 540.3 [M−Cl]$^+$. To a mixture of the succinimidyl activated ester (1.8 g, 3.12 mmol) and 6-aminocaproic acid (0.41 g, 3.12 mmol) in dry DMF (30 mL), triethylamine (1.32 mL, 9.37 mmol) was added. The reaction mixture was stirred under a N$_2$ atmosphere at room temperature overnight. DMF was removed under reduced pressure and the product 9 was purified by flash chromatography (15% methanol in DCM) in 96% yield. $^1$H-NMR (600 MHz, CD$_3$OD) δ 7.95 (s, 1H), 7.82-7.84 (m, 1H), 7.47-7.50 (m, 2H), 6.99-7.01 (m, 1H), 6.40 (d, 2H, J=2.4 Hz), 6.27-6.32 (m, 4H), 3.32-3.36 (q, 8H, J=7.2 Hz), 3.02 (m, 2H), 2.03 (t, 2H, J=7.8 Hz), 1.27-1.30 (m, 2H), 1.12 (t, 12H, J=7.2 Hz), 1.02-1.06 (m, 4H); $^{13}$C NMR (100 MHz, CD$_3$OD) δ 176.8, 168.5, 163.7, 153.7, 153.6, 149.1, 132.8, 131.4, 128.7, 128.3, 123.9, 122.3, 108.3, 105.3, 97.8, 65.7, 44.2, 39.9, 35.9, 33.5, 30.6, 27.8, 26.4, 24.4; ESI-MS: m/z: calcd for C$_{34}$H$_{42}$N$_3$O$_4$: 556.3. found: 556.3 [M+H]$^+$.

Rhodamine B ACA APTES Conjugate (2). To a mixture of rhodamine B ACA Conjugate 9 (750 mg, 1.25 mmol) and APTES (305 mg, 1.38 mmol) in dry DCM (25 mL) EDC (360 mg, 1.88 mmol) was added. The reaction mixture was stirred under a N$_2$ atmosphere at room temperature overnight. Solvent was evaporated and the product 2 was purified by flash chromatography (15% methanol in DCM) in 65% yield. $^1$H-NMR (400 MHz, CDCl$_3$) δ 7.87-7.89 (m, 1H), 7.40-7.43 (m, 2H), 7.05-7.08 (m, 1H), 6.37-6.43 (m, 4H), 6.26-6.28 (m, 2H), 6.07-6.12 (m, 1H), 3.81 (q, 6H, J=7.2 Hz), 3.34 (q, 8H, J=7.2 Hz), 3.18-3.23 (m, 2H), 3.08-3.14 (m, 2H), 2.01 (t, 2H, J=7.2 Hz), 1.57-1.65 (m, 2H), 1.41-1.48 (m, 2H), 1.13-1.23 (m, 24H), 0.63 (t, 2H, J=8.0 Hz); $^{13}$C-NMR (100 MHz, CDCl$_3$) δ 173.0, 168.1, 153.6, 153.3, 148.7, 132.2, 131.4, 128.9, 127.9, 123.7, 122.6, 108.1, 105.8, 97.8, 64.9, 58.4, 50.4, 44.4, 41.9, 39.9, 36.5, 27.7, 26.5, 25.0, 23.0, 18.3; 12.6, 7.8; ESI-MS: m/z: calcd for C$_{43}$H$_{63}$N$_4$O$_6$Si: 759.6. found: 759.8 [M+H]$^+$, calcd for C$_{43}$H$_{62}$N$_4$O$_6$SiNa: 781.4. found: 781.7 [M+Na]$^+$.

Rhodamine B triACA (12). To a mixture of rhodamine B ACA conjugate 9 (367 mg, 0.612 mmol) and N-hydroxysuccinimide (77.5 mg, 0.674 mmol) in dry DCM (20 mL) EDC (176 mg, 0.919 mmol) was added. The reaction mixture was stirred under a N$_2$ atmosphere at room temperature overnight. Solvent was evaporated and the succinimidyl activated ester product was purified by flash chromatography (1:10 methanol/DCM) in 95% yield. $^1$H NMR (400 MHz, CDCl$_3$) δ 7.88-7.90 (m, 1H), 7.42-7.44 (m, 2H), 7.07-7.10 (m, 1H), 6.43 (s, 1H), 6.41 (s, 1H), 6.38 (m, 2H), 6.25-6.28 (dd, 2H, J=6.0, 9.0 Hz), 3.34 (q, 8H, J=7.2 Hz), 3.12 (t, 2H, J=7.2 Hz), 2.81 (s, 4H), 2.39 (t, 2H, J=7.2 Hz), 1.50-1.53 (m, 2H), 1.16 (t, 12H, J=7.2 Hz); $^{13}$C-NMR (100 MHz, CDCl$_3$) δ 169.1, 168.5, 168.0, 153.4, 148.8, 132.2, 131.6, 129.0, 127.9, 123.7, 122.7, 108.0, 106.0, 97.7, 64.8, 44.4, 39.9, 30.6, 27.6, 26.3, 25.6, 24.1, 12.6; ESI-MS: m/z: calcd for C$_{38}$H$_{45}$N$_4$O$_6$: 653.3. found: 653.4 [M+H]$^+$.

To a mixture of succinimidyl activated ester (300 mg, 0.435 mmol) and amino acid 6 (0.41 g, 0.435 mmol) in dry DMF (5 mL), triethylamine (0.25 mL, 1.74 mmol) was added. The reaction mixture was stirred under a N$_2$ atmosphere at room temperature overnight. DMF was removed under reduced pressure and the product rhodamine B triACA 12 was purified by flash chromatography (15% methanol in DCM) in 84% yield. $^1$H NMR (600 MHz, CD$_3$OD) δ 7.96 (s, 2H), 7.81-7.83 (m, 1H), 7.47-7.48 (m, 2H), 6.98-7.00 (m, 1H), 6.40-6.41 (d, 1H), 6.27-6.32 (m, 3H), 3.34 (q, 8H, J=7.2 Hz), 3.12-3.15 (m, 2H); 3.07-3.10 (m, 2H), 3.01-3.05 (t, 2H), 2.25-2.30 (m, 2H), 2.13-2.16 (m, 2H), 1.94-1.97 (m, 2H), 1.56-1.61 (m, 4H), 1.43-1.50 (m, 4H), 1.27-1.34 (m, 6H), 1.10-1.13 (t, 12H, J=7.2 Hz), 1.04-1.05 (m, 4H); $^{13}$C NMR (100 MHz, CD$_3$OD) δ 174.8, 168.6, 153.7, 153.7, 153.6, 150.7, 149.2, 132.8, 131.3, 128.5, 128.3, 123.9, 122.3, 109.9, 108.4, 105.3, 97.9, 65.9, 65.8, 39.9, 39.0, 37.9, 35.8, 33.7, 33.5, 29.0, 27.8, 26.6, 26.4, 26.3, 25.5, 25.2, 24.6, 24.5, 13.6, 11.8; ESI-MS: m/z: calcd for C$_{46}$H$_{64}$N$_5$O$_6$: 782.49. found: 782.9 [M+H]$^+$, calcd for C$_{46}$H$_{63}$N$_5$O$_6$Na: 804.5. found: 804.8 [M+Na]$^+$.

Rhodamine B TriACA APTES Conjugate (3). To a mixture of 12 (200 mg, 0.244 mmol) and APTES (65 mg, 0.293 mmol) in dry DCM (10 mL) EDC (70 mg, 0.366 mmol) was added. The reaction mixture was stirred under a N$_2$ atmosphere at room temperature overnight. Solvent was evaporated and the product 3 was purified by flash chromatography (10% methanol in DCM) in 55% yield. $^1$H-NMR (400 MHz, CDCl$_3$) δ 7.78-7.81 (m, 1H), 7.37-7.42 (m, 2H), 7.02-7.04 (m, 1H), 6.47-6.50 (bs, 1H), 6.16-6.38 (m, 5H), 3.76 (q, 8H, J=7.2 Hz), 3.29 (q, 6H, J=6.8 Hz), 3.02-3.20 (m, 10H), 2.23-3.36 (m, 1H), 2.09-2.15 (m, 4H), 1.95-1.99 (m, 2H), 1.53-1.62 (m, 6H), 1.34-1.49 (m, 7H), 1.03-1.33 (m, 28H), 0.56-0.60 (m, 2H); $^{13}$C-NMR (100 MHz, CDCl$_3$) δ 173.4, 173.2, 171.1, 168.3, 168.2, 162.7, 132.5, 132.4, 129.0, 128.3, 128.2, 124.0, 122.6, 108.2, 105.8, 98.0, 77.0, 58.6, 50.6, 44.5, 42.2, 40.1, 39.4, 38.4, 36.7, 36.6, 35.2, 34.0, 31.6, 29.4, 27.8, 26.7, 26.6, 25.8, 25.6, 25.5, 25.2, 24.7, 23.8, 23.0, 18.5, 14.8, 12.7, 8.0; ESI-MS; m/z: calcd for C$_{55}$H$_{85}$N$_6$O$_8$Si: 985.6. found: 986.1 [M+H]$^+$ Rhodamine B PentaACA (13). To a mixture of rhodamine B ACA conjugate 9 (367 mg, 0.612 mmol) and N-hydroxysuccinimide (77.5 mg, 0.674 mmol) in dry DCM (20 mL) EDC (176 mg, 0.919 mmol) was added. The reaction mixture was stirred under a N$_2$ atmosphere at room temperature overnight. Solvent was evaporated and the succinimidyl activated ester product was purified by flash chromatography (1:10 methanol/DCM) in 95% yield. To a mixture of rhodamine B ACA succinimidyl ester (200 mg, 0.29 mmol) and amino acid 7 (170 mg, 0.29 mmol) in dry DMF (10 mL), triethylamine (0.16 mL, 0.116 mmol) was added. The reaction mixture was stirred under a N$_2$ atmosphere at room temperature overnight. DMF was removed under reduced pressure and the product 13 was purified by flash chromatography (15% methanol in DCM) in 69% yield. $^1$H-NMR (400 MHz, CDCl$_3$) δ 7.82-7.85 (m, 1H), 7.42-7.45 (m, 2H), 7.14-7.18 (m, 1H), 7.06-7.09 (m, 3H), 6.67-6.72 (m, 1H), 6.36-6.40 (m, 4H), 6.24-6.29 (m, 2H), 3.42-3.46 (s, 1H), 3.30-3.36 (q, 8H, J=6.4 Hz), 3.14-3.24 (m, 8H), 3.00-3.13 (m, 2H), 2.30-2.36 (m, 2H), 2.17-2.21 (m, 6H), 2.01-2.07 (m, 2H), 1.57-1.66 (m, 8H), 1.10-1.52 (m, 30H); $^{13}$C-NMR (100 MHz, CDCl$_3$) δ 175.9, 173.8, 173.7, 173.6, 168.3, 153.6, 153.3, 148.8, 132.5, 131.1, 128.7, 128.1, 123.9, 122.5, 108.1, 105.5, 76.8, 65.2, 50.3, 44.4, 40.0, 39.2, 36.3, 36.2, 34.1, 29.2, 29.1, 29.0, 27.7, 26.5, 26.4, 26.3, 25.4, 25.2, 24.5, 12.6; ESI-MS: m/z: calcd for $C_{58}H_{84}N_7O_8$: 1007.65. found: 1007.0 [M−H]$^-$, calcd for $C_{58}H_{85}N_7O_8Na$: 1030.6. found: 1031.1 [M+Na]$^+$.

Rhodamine B PentaACA APTES Conjugate (4). To a mixture of 13 (200 mg, 0.191 mmol) and APTES (47 mg, 0.211 mmol) in dry DCM (15 mL) EDC (55 mg, 0.287 mmol) was added. The reaction mixture was stirred under a $N_2$ atmosphere at room temperature overnight. Solvent was evaporated and the product 4 was purified by flash chromatography (15% methanol in DCM) in 70% yield. $^1$H-NMR (600 MHz, $CDCl_3$) δ 7.81-7.83 (m, 1H), 7.42-7.44 (m, 2H), 7.07-7.09 (m, 1H), 6.99 (t, 1H, J=5.4 Hz), 6.93-6.96 (m, 3H), 6.65 (t, 1H, J=5.4 Hz), 6.54 (t, 1H, J=5.4 Hz), 6.34-6.40 (m, 4H), 6.27 (dd, 2H, J=9.0, 2.4 Hz), 3.81 (q, 6H, J=7.2 Hz), 3.34 (q, 8H, J=7.2 Hz), 3.16-3.22 (m, 10H), 3.10 (t, 2H, J=6.6 Hz), 2.16-2.19 (m, 8H), 2.02 (t, 2H, J=7.2 Hz), 1.58-1.66 (m, 8H), 1.46-1.54 (m, 8H), 1.38-1.44 (m, 2H), 1.28-1.36 (m, 8H), 1.21 (t, 9H, J=7.2 Hz), 1.16 (t, 12H, J=7.2 Hz), 1.07-1.14 (m, 6H), 0.63 (t, 2H, J=8.4 Hz); $^{13}$C-NMR (100 MHz, $CDCl_3$) δ 173.3, 173.2, 173.1, 168.1, 153.6, 153.3, 148.8, 132.4, 131.2, 128.8, 128.0, 123.9, 122.4, 108.0, 105.6, 97.8, 65.1, 58.4, 44.4, 42.0, 40.0, 39.2, 36.5, 36.4, 29.4, 29.3, 27.8, 26.7, 26.6, 26.5, 26.4, 25.4, 25.2, 23.0, 18.3, 12.6, 7.9; ESI-MS: m/z: calcd for $C_{67}H_{106}N_8O_{10}SiNa$: 1233.8. found: 1234.0 [M+Na]$^+$ p-Nitrobenzyl 3,4,6-tri-O-acetyl-2-deoxy-2-phthalimido-β-D-glucopyranoside (16). A mixture of 1,3,4,6-Tetra-O-acetyl-2-phthalimido-2-deoxy-D-glucopyranoside (15) (3 g, 0.628 mmol), p-nitrobenzyl alcohol (1.06 g, 0.691 mmol) and activated MS-A W-300 in DCM (50 mL) was stirred at 0° C. under a $N_2$ atmosphere for 30 minutes. $SnCl_4$ (6.548 g, 2.51 mmol) was added dropwise using a syringe. Yellow coloration was seen. The mixture was stirred at room temperature overnight. The mixture was filtered through celite, washed successively with ice cold 2M aqueous $H_2SO_4$ solution, saturated aqueous $NaHCO_3$ solution and brine. The organic layer was dried over anhydrous $Na_2SO_4$ and concentrated under reduced pressure. Flash column chromatography using hexanes/EtOAc (1:1) gave the pure title compound in 86% yield. $^1$H-NMR (600 MHz, $CDCl_3$) δ 7.91-7.93 (m, 2H), 7.7-7.78 (m, 4H), 7.20-7.28 (m, 2H), 5.76 (dd, 1H, J=9.6, 10.8 Hz), 5.41 (d, 1H, J=8.4 Hz), 5.18 (dd, 1H, J=9.6, 9.6 Hz), 4.93 (d, 1H, J=13.2 Hz), 4.59 (d, 1H, J=13.2 Hz), 4.37 (dd, 1H, J=8.4, 10.8 Hz), 4.32 (dd, 1H, J=4.8, 12.0 Hz), 4.17 (dd, 1H, J=1.8, 12.0 Hz), 3.86-3.88 (m, 1H), 2.1 (s, 3H), 2.0 (s, 3H), 1.84 (s, 3H); $^{13}$C-NMR (100 MHz, $CDCl_3$) δ 170.9, 170.3, 169.7, 147.6, 144.4, 134.7, 131.4, 128.2, 123.8, 123.7, 98.0, 77.2, 70.7, 70.4, 68.9, 62.1, 54.8, 21.0, 20.8, 20.6; ESI-MS: m/z: calcd for $C_{27}H_{26}N_2O_{12}Na$: 593.1. found: 593.2 [M+Na]$^+$.

p-Nitrobenzyl 4,6-O-benzylidene-2-deoxy-2-phthalimido-β-D-glucopyranoside (17). A solution of compound 16 (3 g, 5.25 mmol) in anhydrous DCM (30 mL) was cooled to −10° C. under a nitrogen atmosphere. Freshly prepared sodium methoxide solution [sodium (48 mg, 2.10 mmol) in dry methanol (30 mL)] was added slowly to the reaction mixture and stirred at 0° C. for 3 hours. Reaction mixture was neutralized by adding amberlyst IR 120 resin and filtered. Solvents were removed at reduced pressure to get p-nitrobenzyl 2-deoxy-2-phthalimido-β-D-glucopyranoside in 98% yield. $^1$H-NMR (600 MHz, $CD_3OD$) δ 7.86-7.90 (m, 2H), 7.60-7.84 (m, 4H), 7.24-7.32 (m, 2H), 5.18 (d, 1H, J=9.0 Hz), 4.92 (d, 1H, J=13.2 Hz), 4.65 (d, 1H, J=13.2 Hz), 4.23 (dd, 1H, J=9.0, 10.8 Hz), 4.04 (dd, 1H, J=9.0, 10.8 Hz), 3.94 (dd, 1H, J=2.4, 12.0 Hz), 3.75 (dd, 1H, J=5.4, 12.0 Hz), 3.38-3.46 (m, 2H); $^{13}$C-NMR (100 MHz, $CD_3OD$) δ 148.3, 146.2, 135.3, 132.5, 129.1, 124.1, 98.9, 78.0, 72.2, 72.0, 70.5, 62.5, 58.2; ESI-MS: m/z: calcd for $C_{21}H_{20}N_2O_9Na$: 467.1. found: 467.1 [M+23]$^+$. p-Nitrobenzyl 2-deoxy-2-phthalimido-β-D-glucopyranoside (1.5 g, 0.031 mol) was azeotropically refluxed with toluene (100 mL) using a Dean-Stark apparatus for 3 hours. Then temperature was lowered down to 90° C. At this temperature, DL-camphorsulfonicacid (0.844 mmol) was added followed by benzaldehyde dimethylacetal (0.54 g, 0.035 mol). After 30 minutes, the temperature was raised to reflux temperature. The reaction was quenched by adding triethylamine. Solvents were removed under reduced pressure. Residue was extracted in ethyl acetate and washed with saturated brine. The organic layer was dried over anhydrous $Na_2SO_4$ and concentrated under reduced pressure. Flash column chromatography using hexanes/ethyl acetate (2:3) gave the pure compound 17 in 82% yield. $^1$H NMR (400 MHz, $CDCl_3$) δ 7.86-7.90 (m, 2H), 7.68 (m, 4H), 7.46-7.49 (m, 2H), 7.33-7.35 (m, 3H), 7.20-7.26 (m, 2H), 5.56 (s, 1H), 5.27 (d, 1H, J=8.8 Hz), 4.91 (d, 1H, J=13.6 Hz), 4.57 (m, 2H), 4.38 (dd, 1H, J=4.0, 10.4 Hz), 4.27 (dd, 1H, J=8.8, 10.4 Hz), 3.79-3.85 (m, 1H), 3.56-3.65 (m, 2H), 2.98 (d, 1H, J=4.0 Hz); $^{13}$C-NMR (100 MHz, $CDCl_3$) δ 147.5, 144.6, 137.1, 134.6, 131.6, 129.7, 128.7, 128.1, 126.5, 123.8, 102.2, 98.7, 82.3, 70.3, 68.8, 68.7, 66.5, 56.7; ESI-MS: m/z: calcd for $C_{28}H_{24}N_2O_9Na$: 555.1. found: 555.2 [M+Na]$^+$.

p-Aminobenzyl 3-(4-oxo-pentanoyl)-4,6-O-benzylidene-2-deoxy-2-phthalimido-β-D-gluco-pyranoside (18). The mixture of compound 17 (1 g, 1.32 mmol), 4-oxopentanoic acid (0.31 g, 2.64 mmol), dicyclohexylcarbodiimide (0.55 g, 2.64 mmol) and DMAP (32 mg, 0.26 mmol) in anhydrous DCM were stirred at room temperature overnight under a nitrogen atmosphere. Solvent was removed under reduced pressure and the residue was extracted in ethyl acetate. The precipitated dicyclohexyl urea was removed by filtration and ethyl acetate extract was washed with saturated brine. The organic layer was dried over anhydrous $Na_2SO_4$ and concentrated under reduced pressure. Flash column chromatography using hexanes/ethyl acetate (1:2) gave the pure compound p-nitrobenzyl 3-(4-oxo-pentanoyl)-4,6-O-benzylidene-2-deoxy-2-phthalimido-β-D-glucopyranoside in 81% yield. $^1$H-NMR (600 MHz, $CDCl_3$) δ 7.85-7.92 (m, 1H), 7.66-7.86 (m, 4H), 7.43-7.45 (m, 2H), 7.32-7.36 (m, 3H), 7.20-7.28 (m, 1H), 5.91 (dd, 1H, J=8.4, 10.8 Hz), 5.54 (s, 1H), 5.43 (d, 1H, J=8.4 Hz), 4.93 (d, 1H, J=13.8 Hz), 4.59 (d, 1H, J=13.8 Hz), 4.42 (dd, 1H, J=4.2, 10.2 Hz), 4.36 (dd, 1H, J=8.4, 10.2 Hz), 3.85 (t, 1H, J=9.6 Hz), 3.79 (t, 1H, J=9.0 Hz), 3.72-3.78 (m, 1H), 2.50-2.56 (m, 1H), 2.34-2.46 (m, 3H), 1.85 (s, 3H); $^{13}$C NMR (100 MHz, $CDCl_3$) δ 206.0, 172.2, 147.5, 144.5, 137.0, 134.4, 129.4, 128.5, 128.1, 126.5, 123.7, 101.8, 98.7, 79.4, 70.6, 69.6, 68.8, 68.2, 66.6, 55.3, 37.9, 29.6, 28.0, 25.8; ESI-MS: m/z: calcd for $C_{33}H_{30}N_2O_{11}Na$: 653.2. found: 653.3 [M+Na]$^+$. A round bottom flask was charged with palladium acetate (18 mg, 0.08 mmol), p-nitrobenzyl 3-(4-oxo-pentanoyl)-4,6-O-benzylidene-2-deoxy-2-phthalimido-β-D-glucopyranoside (1 g, 1.58 mmol) and dry THF (20 mL). The flask was sealed and purged with nitrogen. An aqueous solution of KF (184 mg, 3.17 mmol in 4 mL of degassed water) was added via a syringe. Triethylsilane (1.02 mL, 6.34 mmol) was slowly added dropwise with a syringe (caution: rapid addition of triethylsilane can result in uncontrollable gas evolution). The reaction mixture was stirred at room temperature for 1 hour under nitrogen atmosphere. After completion of the reaction as indicated by TLC, flask was opened to air, diluted with diethyl ether (20 mL) and stirred for 5 minutes. The layers were separated and aqueous layer was back extracted with diethyl ether. The combined organic layers were filtered though a pad of celite. The filtrate was concentrated and purified by flash column chromatography using hexanes/ethyl acetate (1:2) gave the pure compound 18 in 76% yield. $^1$H-NMR (600 MHz, CDCl$_3$) δ 7.67-7.81 (m, 4H), 7.43 (d, 2H), 7.31-7.33 (m, 3H), 6.75-6.80 (m, 2H), 6.20-6.28 (m, 2H), 5.91 (t, 1H, J=9.6 Hz), 5.52 (s, 1H), 5.35 (d, 1H, J=9.6 Hz), 4.67 (d, 1H, J=11.4 Hz), 4.40 (dd, 1H, J=4.8, 11.4 Hz), 4.36 (d, 1H, J=11.4 Hz), 4.29 (t, 1H, J=9.6 Hz); 3.83 (t, 1H, J=10.2 Hz), 3.68-3.76 (m, 2H), 3.54 (bs, 2H), 2.33-2.52 (m, 4H), 1.84 (s, 3H); $^{13}$C-NMR (100 MHz, CDCl$_3$) δ 206.0, 172.1, 167.9, 146.6, 137.2, 134.1, 131.8, 129.7, 129.3, 128.5, 126.5, 126.4, 123.6, 114.9, 101.7, 97.6, 79.6, 71.8, 68.9, 68.9, 66.3, 55.4, 38.0, 29.6, 28.1; ESI-MS: m/z: calcd for C$_{33}$H$_{32}$N$_2$O$_9$Na: 623.2. found: 623.4 [M+Na]$^+$.

p-(4-O-Benzyloxycarbonyl-propionylamino)-benzyl 3-(4-oxo-pentanoyl)-4,6-O-benzylidene-2-deoxy-2-phthalimido-β-D-glucopyranoside (19). A mixture of compound 18 (1 g, 1.66 mmol), O-benzylsuccinate (416 mg, 2.0 mmol), BOP reagent (884 mg, 2.0 mmol) and N,N-diisopropylethylamine (0.87 mL, 5.0 mmol) in anhydrous DCM (40 mL) was stirred at room temperature for 48 hours under a nitrogen atmosphere. The reaction mixture was washed with 1N aqueous HCl and saturated brine. The organic layer was dried over anhydrous Na$_2$SO$_4$ and concentrated under reduced pressure. Flash column chromatography using hexanes/ethyl acetate (1:2) gave the pure compound 19 in 67% yield. $^1$H-NMR (600 MHz, CDCl$_3$) δ 7.63-7.79 (m, 5H), 7.43-7.45 (m, 2H), 7.28-7.35 (m, 8H), 7.09-7.16 (m, 2H), 6.90-6.95 (m, 2H), 5.94 (dd, 1H, J=9.0, 10.2 Hz), 5.53 (s, 1H), 5.35 (d, 1H, J=7.8 Hz), 5.11 (s, 2H), 4.73 (d, 1H, J=12.0 Hz), 4.40-4.44 (m, 2H), 4.32 (dd, 1H, J=8.4, 10.2 Hz), 3.85 (t, 1H, J=9.6 Hz), 3.71-3.78 (m, 2H), 2.72 (t, 2H, J=6.6 Hz), 2.56 (t, 2H, J=6.6 Hz), 2.34-2.53 (m, 4H), 1.85 (s, 3H); $^{13}$C-NMR (100 MHz, CDCl$_3$) δ 206.2, 173.14, 172.2, 169.7, 138.0, 137.1, 135.9, 134.3, 132.3, 129.4, 128.9, 128.8, 128.6, 128.5, 128.4, 126.4, 123.7, 119.5, 101.7, 97.7, 79.5, 71.4, 69.8, 68.9, 66.9, 66.4, 55.3, 37.9, 32.0, 29.6, 29.5, 28.1 ESI-MS: m/z: calcd for C$_{44}$H$_{42}$N$_2$O$_{12}$Na: 813.3. found: 813.5 [M+23]$^+$.

p-[4-(N-(3-Triethoxysilylpropylamino)succinamido)]-benzyl 4,6-O-benzylidene-2-deoxy-2-phthalimido-β-D-glucopyranoside (14). A mixture of compound 19 (1 g, 1.26 mmol) and hydrazine acetate (467 mg, 5.05 mmol) in DCM/MeOH (1:1, 100 mL) was stirred at room temperature for 3 hours. Solvents were removed under reduced pressure and purified by flash column chromatography using hexanes/ethyl acetate (1:2) gave the pure compound p-(4-O-benzyloxycarbonyl-propionylamino-benzyl)-4,6-O-benzylidene-2-deoxy-2-phthalimido-β-D-glucopyranoside in 90% yield. $^1$H NMR (400 MHz, CDCl$_3$) δ 7.66-7.75 (m, 4H), 7.46-7.49 (m, 3H), 7.3-7.39 (m, 8H), 7.11-7.19 (m, 2H), 6.96-7.02 (m, 2H), 5.56 (s, 1H), 5.24 (d, 1H, J=9.0 Hz), 5.13 (s, 2H), 4.76 (d, 1H, J=12.6 Hz), 4.62 (dd, 1H, J=9.0, 10.2 Hz), 4.44 (d, 1H, J=12.6 Hz), 4.41 (dd, 1H, J=4.2, 10.2 Hz), 4.26 (dd, 1H, J=9.0, 10.2 Hz), 3.84 (t, 1H, J=10.2 Hz), 3.59-3.65 (m, 2H), 2.77 (t, 2H, J=6.6 Hz), 2.60 (t, 2H, J=6.6 Hz); $^{13}$C-NMR (100 MHz; CDCl$_3$) δ 173.1, 169.6, 168.1, 137.6, 137.0, 135.5, 134.1, 132.3, 131.3, 129.3, 128.6, 128.5, 128.3, 128.1, 126.3, 123.3, 119.3, 101.8, 97.8, 82.0, 70.9, 68.6, 68.3, 66.7, 66.1, 56.8, 31.7, 29.3; ESI-MS: m/z: calcd for C$_{39}$H$_{36}$N$_2$O$_{10}$Na: 715.2. found: 715.5 [M+Na]$^+$. A mixture of compound p-(4-O-benzyloxycarbonyl-propionylamino-benzyl)-4,6-O-benzylidene-2-deoxy-2-phthalimido-β-D-glucopyranoside (600 mg) and palladium on activated charcoal (10%) (1.2 g) in dry methanol (50 mL) was stirred under a hydrogen atmosphere at room temperature for 30 minutes. The reaction mass was filtered through celite and concentrated to get the carboxylic acid in 98% yield. $^1$H NMR (400 MHz, CD$_3$OD) δ 7.63-7.79 (m, 4H), 7.49-7.62 (m, 2H), 7.32-7.52 (m, 2H), 7.16 (d, 2H, J=8.4 Hz), 6.94 (d, 1H, J=8.4 Hz), 5.62 (s, 1H), 5.22 (d, 1H, J=8.4 Hz), 4.68 (d, 1H, J=12.4 Hz), 4.50-4.55 (m, 1H), 4.43 (d, 1H, J=12.4 Hz), 4.37 (dd, 1H, J=4.4, 10.4 Hz), 4.08 (dd, 1H, J=8.8, 10.4 Hz), 3.83-3.88 (m, 1H), 3.58-3.63 (m, 2H), 2.62 (s, 4H); $^{13}$C NMR (100 MHz, CD$_3$OD) δ 171.7, 168.3, 138.5, 137.8, 134.4, 132.6, 131.5, 128.8, 128.6, 127.9, 126.4, 123.1, 119.3, 101.8, 98.2, 81.9, 71.1, 68.5, 68.0, 66.7, 65.4, 57.8, 53.7, 31.6, 29.6; ESI-MS: m/z: calcd for C$_{32}$H$_{30}$N$_2$O$_{10}$Na: 625.2. found: 625.3 [M+Na]$^+$. A mixture of the carboxylic acid obtained (500 mg, 0.83 mmol), APTES (275 mg, 1.24 mmol) and EDC (239 mg, 1.24 mmol) in anhydrous DCM (15 mL) was stirred at room temperature under a nitrogen atmosphere for 5 hours. Solvent was removed under reduced pressure and the crude product was purified by flash column chromatography (10% methanol in DCM) producing the pure compound 14 in 77% yield. $^1$H NMR (600 MHz, CDCl$_3$) δ 8.77 (s, 1H), 7.63-7.70 (m, 4H), 7.46-7.47 (m, 2H), 7.32-7.34 (m, 3H), 7.14-7.19 (m, 2H), 6.88-6.94 (m, 2H), 6.23 (m, 1H), 5.55 (s, 1H), 5.23 (d, 1H, J=8.4 Hz), 4.73 (d, 1H, J=12.0 Hz), 4.61 (m, 1H), 4.40 (t, 2H, J=9.0 Hz), 4.24 (t, 1H, J=9.0 Hz), 3.73-3.85 (m, 8H), 3.61-3.63 (m, 2H), 3.38 (s, 1H), 3.14-3.16 (m, 2H), 2.59 (t, 2H, J=5.4 Hz), 2.48 (t, 2H, J=5.4 Hz), 1.53-1.58 (m, 2H), 1.18 (t, 9H, J=7.2 Hz), 0.57 (t, 2H, J=7.2 Hz); $^{13}$C NMR (100 MHz, CDCl$_3$) δ 172.4, 170.5, 168.1, 137.9, 137.1, 134.1, 132.2, 131.5, 129.3, 128.5, 128.3, 126.3, 123.4, 119.4, 101.9, 97.8, 82.1, 71.0, 68.7, 68.4, 66.2, 58.6, 58.5, 56.9, 42.1, 32.8, 31.5, 2.7, 18.3, 7.8 ESI-MS: m/z: calcd for C$_{41}$H$_{51}$N$_3$O$_{12}$SiNa: 828.3. found: 828.7 [M+Na]$^+$.

Kits embodying the methods and comprising various components of the device/apparatus/integrated systems herein are also provided. Multiple uses of the methods and/or device/systems for any of the purposes indicated herein are also a feature of the invention.

The system described herein can optionally include a means for contacting the particles with reagents and analytes. Also, the system can optionally include a computer operably linked thereto and the detection means for the acquisition and analysis of a signal generated by the detection means. The system can also optionally include a data analysis means for converting the signal to the identity of the nanoparticle and optionally the presence or degree of binding of an analyte or group of analytes to the nanoparticle. The data analysis means can further be configured to detect binding of or identifying the analyte or group of analytes.

The system described herein can optionally include a computer-readable medium having computer-executable instructions for performing the steps described herein. Also, the system can optionally include a programmed computer system for detecting MNPs comprising: measuring a plasmon enhancement of a magneto-optical response.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration, and not limitation of the following claims.

What is claimed is:

1. A system for detecting magnetic particles, comprising a sensing material having a matrix having implanted, deposited or patterned therein one or more magnetic nanoparticles or thin films, wherein the nanoparticles include a glycoconjugate having a carbohydrate molecule or a carbohydrate moiety, and a reactive spacer structure moiety in the glycoconjugate, and wherein the reactive spacer structure moiety interacts with a surface of the nanoparticle;
   the matrix being capable of allowing the magnetic metallic nanoparticles to exhibit plasmon-like resonances and magneto-optical properties, and having binding nanoparticles deposited on the surface of the sensing material.

2. The system of claim 1, wherein the binding nanoparticles comprise glyco-nanoparticles.

3. The system of claim 1, wherein the system further includes glyco-nanoparticles bound to one or more agents.

4. The system of claim 1, wherein the implanting or patterning includes one or more of at least partially embedding the magnetic metallic nanoparticles in the matrix, or at least partially coating the magnetic metallic nanoparticles on the matrix.

5. The system of claim 1, wherein the matrix comprises one or more of a metal, glass or other dielectric substrate.

6. The system of claim 1, wherein the system detects one or more agents in a medium, the magnetic glyco-nanoparticles being capable of binding to one or more agents in the medium.

7. The system of claim 6, wherein the agent comprises a pathogen.

8. The system of claim 1, wherein the system comprises an array having nanoclusters of the magnetic nanoparticles embedded on a metallic or dielectric thin film matrix.

9. The system of claim 1, wherein the magnetic nanoparticles are functionalized with organic molecules comprising using a direct attachment approach.

10. The system of claim 1, wherein the system comprises a coated substrate having deposited thereon magnetic nanoparticles at an outer surface of the film.

11. The system of claim 1, wherein Co ions are implanted on epitaxial Au thin films, or wherein patterned Co films are deposited onto Au films.

12. The system of claim 1, wherein the system is comprised of nanoclusters where one or more of a size and an interparticle distance of the nanoparticles in the nanoclusters is varied.

13. The system of claim 1, wherein a solution of coated ferromagnetic nanoparticles has been used to deposit binding nanoparticles of an outer surface of a thin film.

14. A system for detecting magnetic particles, comprising a sensing material having a matrix having implanted, deposited or patterned therein one or more magnetic nanoparticles or thin films, wherein the nanoparticles include a glycoconjugate having a carbohydrate molecule or a carbohydrate moiety, and a reactive spacer structure moiety in the glycoconjugate, and wherein the reactive spacer structure moiety interacts with a surface of the nanoparticle;
   the matrix being capable of allowing the magnetic metallic nanoparticles to exhibit plasmon-like resonances and magneto-optical properties, and having binding nanoparticles deposited on the surface of the sensing material;
   wherein the reactive spacer structure moiety comprises a hydrophilic linker.

15. A system for detecting magnetic particles, comprising:
   a sensing material having a matrix having implanted, deposited or patterned therein one or more magnetic nanoparticles or thin films, wherein the nanoparticles include a glycoconjugate having a carbohydrate molecule or a carbohydrate moiety, and a reactive spacer structure moiety in the glycoconjugate, and wherein the reactive spacer structure moiety interacts with a surface of the nanoparticle;
   the matrix being capable of allowing the magnetic metallic nanoparticles to exhibit plasmon-like resonances and magneto-optical properties, and having binding nanoparticles deposited on the surface of the sensing material;
   wherein the reactive spacer structure moiety comprises a hydrophobic linker.

16. A system for detecting magnetic particles, comprising:
   a sensing material having a matrix having implanted, deposited or patterned therein one or more magnetic nanoparticles or thin films, wherein the nanoparticles include a glycoconjugate having a carbohydrate molecule or a carbohydrate moiety, and a reactive spacer structure moiety in the glycoconjugate;
   the matrix being capable of allowing the magnetic metallic nanoparticles to exhibit plasmon-like resonances and magneto-optical properties, and having binding nanoparticles deposited on the surface of the sensing material;
   wherein one or more glycoconjugates are immobilized onto the magnetic nanoparticles under reductive conditions.

17. The system of claim 16, wherein one or more glycoconjugates are immobilized onto the magnetic nanoparticles using one or more carbohydrates with ferrites and/or transition metals.

18. The system of claim 16, wherein one or more glycoconjugates are immobilized onto the magnetic nanoparticles under reductive conditions using one or more thiolates with metal atoms.

* * * * *